US010655120B2

(12) United States Patent
Connon et al.

(10) Patent No.: US 10,655,120 B2
(45) Date of Patent: May 19, 2020

(54) TRANSPORT OF CELLS IN HYDROGELS

(75) Inventors: Che John Connon, Reading (GB); Richard Anthony Cave, Sheffield (GB); Vitaliy Khutoryanskiy, Reading (GB); Bernice Wright, Reading (GB)

(73) Assignee: The University of Newcastle Upon Tyne, Newcastle upon Tyne (GB)

( * ) Notice: Subject to any disclaimer, the term of this patent is extended or adjusted under 35 U.S.C. 154(b) by 0 days.

(21) Appl. No.: 14/006,369

(22) PCT Filed: Mar. 21, 2012

(86) PCT No.: PCT/GB2012/050612
§ 371 (c)(1),
(2), (4) Date: Nov. 26, 2013

(87) PCT Pub. No.: WO2012/127224
PCT Pub. Date: Sep. 27, 2012

(65) Prior Publication Data
US 2014/0072601 A1 Mar. 13, 2014

Related U.S. Application Data

(60) Provisional application No. 61/454,877, filed on Mar. 21, 2011.

(30) Foreign Application Priority Data

Mar. 21, 2011 (GB) .................................. 1104711.5
Aug. 12, 2011 (GB) .................................. 1113978.9

(51) Int. Cl.
| | |
|---|---|
| *C12N 11/10* | (2006.01) |
| *A61K 35/30* | (2015.01) |
| *A61K 9/06* | (2006.01) |
| *A61K 9/00* | (2006.01) |
| *A01N 1/02* | (2006.01) |
| *A61K 47/36* | (2006.01) |
| *A61L 27/52* | (2006.01) |
| *A61L 27/38* | (2006.01) |
| *A61K 38/18* | (2006.01) |

(52) U.S. Cl.
CPC ............ *C12N 11/10* (2013.01); *A01N 1/0231* (2013.01); *A61K 9/0051* (2013.01); *A61K 9/06* (2013.01); *A61K 35/30* (2013.01); *A61K 38/18* (2013.01); *A61K 47/36* (2013.01); *A61L 27/3834* (2013.01); *A61L 27/52* (2013.01); *A61L 2400/04* (2013.01); *A61L 2430/16* (2013.01)

(58) Field of Classification Search
USPC ........................................................ 424/400
See application file for complete search history.

(56) References Cited

U.S. PATENT DOCUMENTS

| | | | | |
|---|---|---|---|---|
| 3,998,215 | A | * | 12/1976 | Anderson ............ A61B 5/0408 600/391 |
| 4,352,883 | A | * | 10/1982 | Lim ........................ A01N 1/02 264/4 |
| 5,944,754 | A | * | 8/1999 | Vacanti ....................... 623/23.76 |
| 6,541,028 | B1 | | 4/2003 | Kuri-Harcuch et al. |
| 2002/0160471 | A1 | | 10/2002 | Kisiday et al. |
| 2005/0014252 | A1 | | 1/2005 | Chu et al. |
| 2005/0053586 | A1 | | 3/2005 | Conn et al. |
| 2006/0275896 | A1 | | 12/2006 | Anderson et al. |
| 2009/0155885 | A1 | | 6/2009 | Bartsch |

FOREIGN PATENT DOCUMENTS

| | | |
|---|---|---|
| EP | 1266570 | 12/2002 |
| EP | 1416044 | 5/2004 |
| EP | 1637145 | 3/2006 |
| EP | 1930411 | 6/2008 |
| JP | 6141851 | 5/1994 |
| JP | 6153928 | 6/1994 |
| JP | 8009966 | 1/1996 |
| JP | 8023968 | 1/1996 |
| WO | WO 93/17669 | 9/1993 |
| WO | WO 95/19430 | 7/1995 |
| WO | WO 97/17038 | 5/1997 |
| WO | WO 98/23226 | 6/1998 |
| WO | WO2000062829 | * 10/2000 |
| WO | WO2001008630 | * 2/2001 |
| WO | WO 02/49428 | 6/2002 |
| WO | WO 03/039481 | 5/2003 |
| WO | WO 2005/063147 | 7/2005 |
| WO | WO 2006/003442 | 1/2006 |
| WO | WO 2006/042272 | 4/2006 |
| WO | WO 2006/103685 | 10/2006 |
| WO | WO 2007/060459 | 5/2007 |
| WO | WO 2007/089997 | 8/2007 |
| WO | WO 2007/103209 | 9/2007 |
| WO | WO 2009/004351 | 1/2009 |
| WO | WO 2010/069589 | 6/2010 |
| WO | WO 2010/123938 | 10/2010 |

OTHER PUBLICATIONS

Banerjee (Biomaterials 30 (2009) 4695-4699).*
Mohan (Trends Biomater. Artif. Organs, vol. 18 (2), Jan. 2005).*
Ananta, M. et al., "A Poly(Lactic Acid-Co-Caprolactone)-Collagen Hybrid for Tissue Engineering Applications" Tissue Engineering: Part A, 2009, vol. 15, 1667-1675.
Chandia, N. P. et al., "Alginic acids in Lessonia Trabeculata: characterization by formic acid hydrolysis and FT-IR spectroscopy" Carbohydrate Polymers 46, 2001, 81-87.
Chen, B. et al., "A novel alternative to cryo-preservation for the short term storage of stem cells for use in cell therapy using alginate encapsulation" Tissue Engineering Part C: Methods, 2013, 19(7):568-576.

(Continued)

Primary Examiner — Devang K Thakor

(74) Attorney, Agent, or Firm — Michael Best & Friedrich LLP

(57) ABSTRACT

The present invention relates to hydrogels which may be used to encapsulate or entrap live cells. The invention further relates to methods for transporting live cells which are encapsulated or entrapped within hydrogels from a first location to a second location. The invention further relates to method of treating a wound, disease or tissue injury, e.g. an ocular injury or a damaged ocular surface in a subject using a hydrogel comprising corneal stem cells. The hydrogels used in such methods may be ones which have been transported from a first location to a second location.

10 Claims, 16 Drawing Sheets

(56) References Cited

OTHER PUBLICATIONS

Chhatbar, M. et al., "Microwave assisted rapid method for hydrolysis of sodium alginate for M/G ratio determination" Carbohydrate Polymers 76, 2009, 650-656.
Cook, M. T. et al., "CLSM Method for the Dynamic Observation of pH Change within Polymer Matrices for Oral Delivery" Biomacromolecules, 2013, 14, 387-393.
Cook, M. T. et al., "Layer-by-layer coating of alginate matrices with chitosan-alginate for the improved survival and targeted delivery of probiotic bacteria after oral administration" Journal of Materials Chemistry B, 2013, 1, 52-60.
Cook, M. T. et al., "Microencapsulation of a synbiotic into PLGA/alginate multiparticulate gels" International Journal of Pharmaceutics 466, 2014, 400-408.
Cook, M. T. et al., "Microencapsulation of Probiotic Bacteria into Alginate Hydrogels" RSC Soft Matter No. 2, 2014, Chapter 5, 95-111.
Cook, M. T. et al., "Microencapsulation of probiotics for gastrointestinal delivery" Journal of Controlled Release 162, 2012, 56-67.
Cook, M. T. et al., "Production and Evaluation of Dry Alginate-Chitosan Microcapsulates as an Enteric Delivery Vehicle for Probiotic Bacteria" Biomacromolecules 2011, 12, 2834-2840.
Cook, M. T. et al., "Visualising pH within alginate gels using confocal microscopy" 2014, 10-11.
De Barros, J. M. S. et al., "A Laminated Polymer Film Formulation for Enteric Delivery of Live Vaccine and Probiotic Bacteria" Journal of Pharmaceutical Sciences, 2014, 103(7) 2022-32.
Hoemann, C.D. et al., "Cytocompatible gel formation of chitosan-glycerol phosphate solutions supplemented with hydroxyl ethyl cellulose is due to the presence of glyoxal" Journal of Biomedical Materials Research, 2007, 521-529.
Klöck, G. et al., "Biocompatibility of mannuronic acid-rich alginates" Biomaterials 18, 1997, 707-713.
Ma, H. L. et al., "Chondrogenesis of human mesenchymal stem cells encapsulated in alginate beads" Wiley Periodicals, 2002, 273-281.
McLaughlin, C. R. et al., "Bioengineered corneas for transplantation and in vitro toxicology" Frontiers in Bioscience 14, 2009, 3326-3337.
Mi, S. et al., "Ex Vivo Construction of an Artificial Ocular Surface by Combination of Corneal Limbal Epithelial Cells and a Compressed Collagen Scaffold Containing Keratocytes" Tissue Engineering: Part A, 2010, vol. 16, No. 6, 2091-2100.
Mi, S. et al., "Photochemical cross-linking of plastically compressed collagen gel produces an optimal scaffold for corneal tissue engineering" J Biomed Mater Res Part A, 2011, 99A:1-8.
Mørch, "Novel Alginate Microcapsules for Cell Therapy" 2008, 86 pages.
Nualkaekul, S. et al., "Chitosan coated alginate beads for the survival of microencapsulated Lactobacilus plantarum in pomegranate juice" Carbohydrate Polymers 90, 2012, 1281-1287.
Nualkaekul, S. et al., "Influence of encapsulation and coating materials on the survival of Lactobacillus plantarum and Bifidobacterium longum in fruit juices" Food Research International 53, 2012, 304-311.
Sefton, M. V. et al., "Microencapsulation of Erythrocytes" Biochimica et Biophysica Acta, 717, 1982, 473-477.
Timmons, J. et al., "Alginates as haemostatic agents: worth revisiting" Wounds, 2009, vol. 5, No. 4, 122-125.
Tu, Y. et al., "Synthetic elastin hydrogels that are coblended with heparin display substantial swelling, increased porosity, and improved cell penetration" Journal of Biomedical Materials Research Part A, vol. 95(4) 2010, DOI: 10.1002/jbm.a.32950, 1215-1222.
Utheim, T. P. et al., "A novel method for preserving cultured limbal epithelial cells" Br J Ophthalmol, 2007, 91:797-800.
Vrana, N. E. et al., "Cell encapsulation within PVA-based hydrogels via freeze-thawing: a one step scaffold formation and cell storage technique" Journal of Tissue Engineering and Regenerative Medicine, 2009, 3:567-572.
Wong, "Alginates in Tissue Engineering" Methods in Molecular Biology, 2004, vol. 238, 77-86.
Wright, B. et al., "Enhanced viability of corneal epithelial cells for efficient transport/storage using a structurally modified calcium alginate hydrogel" Regen. Med. 2012, 7(3) 295-307.
Wright, B. et al., "Oxidized alginate hydrogels as niche environments for corneal epithelial cells" J Biomed Mater Res A, 2013, 8 pages.
Wright, B. et al., "The Secretome of Alginate-Encapsulated Limbal Epithelial Stem Cells Modulates Corneal Epithelial Cell Proliferation" PLoS ONE, 2013, vol. 8, Issue 7, e70860 (7 pages).
Wright, B. et al., "Towards the use of hydrogels in the treatment of limbal stem cell deficiency" Drug Discovery Today, 2013, vol. 18, Nos. 1-2, 79-86.
Ichii et al. "Shipment of Human Islets for Transplantation", American Journal of Transplantation, (2007, 7, 1010-1020).
Johnson et al., "Quantitative Assessment of Islets of Langerhans Encapsulated in Alginate", Tissue Engineering (Part C 2011, 17, 435-449).

\* cited by examiner

TRANSPORT OF CELLS IN HYDROGELS

CROSS-REFERENCE TO RELATED APPLICATIONS

This patent application is a national stage filing under 35 U.S.C. 371 of International Application No. PCT/GB2012/050612, filed on Mar. 21, 2012, which claims priority to U.S. Provisional Application No. 61/454,877, filed on Mar. 21, 2011; and International Application No. PCT/GB2012/050612, filed on Mar. 21, 2012 also claims foreign priority benefits to United Kingdom Patent Application No. 1104711.5, filed Mar. 21, 2011 and United Kingdom Patent Application No. 1113978.9, filed Aug. 12, 2011, which are incorporated herein by reference in their entireties.

The present invention relates to hydrogels which may be used to encapsulate or entrap live cells. The invention further relates to methods for transporting live cells which are encapsulated or entrapped within hydrogels from a first location to a second location and release of live cells upon reaching the second location. The invention further relates to methods of treating a wound, disease or tissue injury, e.g. an ocular injury or a damaged ocular surface in a subject using a hydrogel comprising corneal stem cells. The hydrogels used in such methods may be ones which have been transported from a first location to a second location.

Although basic cell culture techniques have been used for over 100 years, the development of the biotechnology industry and the more recent industrialisation of these processes has produced a high demand for cell culture products. These products are needed both for biopharmaceutical production and for laboratory-based research.

However, whilst cell culture consumables, for example, media, sera and associated reagents, may readily be transported at room or ambient temperatures, special conditions need to be applied to the transportation of live cells in order to maintain cell viability.

Traditionally, live cells have generally been transported by one of three methods:
(i) Frozen, packed in dry ice. This can require up to 20 kg of dry ice for long journeys.
(ii) Refrigerated. This requires specialised equipment for refrigeration and hence increases distribution costs.
(iii) Cultures at ambient temperature. This requires short transportation times (i.e. of the order of minutes or hours) to avoid significant deterioration of the cell cultures.

It can readily be appreciated, therefore, that all three of the above methods have significant disadvantages.

The invention is based on the use of certain hydrogels. Some hydrogels have previously been used for the storage of living tissues.

For example, EP 1 266 570 A1 relates to the preservation of living organism tissue by coating the tissue with a thermo-reversible hydrogel-forming polymer. Examples of such polymers are given as polypropylene oxide-polyethylene oxide copolymers and polyethylene oxide triol polymers. With regard to other polymers, EP 1 266 570 states that agar gels and alginic acid-type gels have a gel-sol temperature which is too high for use with physiological tissues and that the enzymes required for gel-sol conversion of collagen gels damage living tissues.

JP 8023968A relates to the prevention of cultured skin from being damaged by vibration or inversion by placing the skin in a gelatin sol and then lowering the temperature to convert the sol into gel thereby fixing the skin in the gelatin gel. The gelatin gel is said to provide support for the cultured skin.

WO2010/069589 refers to the use of a homogenous mixture of agarose and agarase for covering or enveloping cells during cell transport. It is noted (Example 2) that the covering or enveloping of cells in this way did not significantly affect the rate of cell proliferation.

The current invention, however, is based, at least in part, upon the recognition that the encapsulation or entrapment of dispersed cells within certain hydrogels not only maintains the viability of the cells encapsulated or entrapped therein, but that it actually suppresses cell division and/or differentiation within those cells at temperatures which include ambient temperature. The recognition of this fact thus facilitates new uses for hydrogels, including the short- and medium-term storage of cells within hydrogels to suppress cell division and/or differentiation, and the use of such hydrogels as carriers for cells during transportation of those cells, e.g. the sending of cells though the post upon request. In particular, this recognition allows the transportation of hydrogels comprising corneal cells from a donor to a recipient, and subsequent methods of treatment of ocular injuries or damaged ocular surfaces in the recipient. Hydrogels comprising other cells types may be used for other treatments, e.g. as a wound dressing.

In particular, the invention demonstrates enhanced mechanical properties which are associated with strontium alginate gels and gels which are reinforced (e.g. with nylon meshes), and improvements in the viability of cells which are immobilised within gels whose pore size has been controlled using a pore size controlling agent such as HEC. Cells may readily be released from such gels, thus facilitating further increased viability rates.

In one aspect therefore, the invention provides a method for transporting cells from a first location to a second location, the method comprising the steps: (i) encapsulating or entrapping the cells in a hydrogel, wherein the hydrogel is in the form of a thin layer or disc; (ii) transporting the cell-containing hydrogel from the first location to the second location; and optionally, (iii) releasing the cells from the hydrogel at the second location.

In a further aspect, the invention provides a method for preparing cells for transportation from a first location to a second location, the method comprising the steps: (i) encapsulating or entrapping the cells in a hydrogel, wherein the hydrogel is in the form of a thin layer or disc; and (ii) packaging the cell-containing hydrogel for transportation from the first location to the second location.

In a further aspect, the invention provides a method for preparing cells for transportation from a first location to a second location, the method comprising the steps: (i) encapsulating or entrapping the cells in a hydrogel, wherein the hydrogel is in the form of a thin layer or disc; (ii) packaging the cell-containing hydrogel; and optionally, (iii) dispatching the cell-containing hydrogel for transportation to the second location.

In yet a further aspect, the invention provides a method for fulfilling an order or request for cells, the method comprising the steps: (i) receiving an order or request for cells; (ii) encapsulating or entrapping the desired cells in a hydrogel, wherein the hydrogel is in the form of a thin layer or disc; (iii) dispatching the cell-containing hydrogel for transportation to the location specified in the order or request; and optionally, (iv) transporting the cell-containing hydrogel to the location specified in the order or request.

In yet a further aspect, the invention provides the use of a hydrogel as a storage medium during the transportation of cells from a first to a second location, wherein the hydrogel is in the form of a thin layer or disc or sheet.

In certain aspects of the invention, there is provided a composition comprising a hydrogel wherein a population of cells is encapsulated or entrapped within the hydrogel. In some embodiments, the composition is packaged in a form suitable for transportation to a remote location.

In other aspects of the invention, there is provided a method of treating an ocular injury in a subject, the method comprising the steps: (a) providing a hydrogel comprising corneal stem cells; (b) contacting the ocular injury with said hydrogel; and optionally (c) securing the said hydrogel at the site of the ocular injury.

The hydrogel referred to herein comprises a hydrogel-forming polymer having a cross-linked or network structure or matrix; and an interstitial liquid. The hydrogel is capable of suppressing or preventing cell division and/or differentiation in cells encapsulated or entrapped therein. Preferably, the hydrogel is semi-permeable.

The term "hydrogel-forming polymer" refers to a polymer which is capable of forming a cross-linked or network structure or matrix under appropriate conditions, wherein an interstitial liquid and cells may be retained within such a structure or matrix. The hydrogel will comprise internal pores.

Initiation of the formation of the cross-linked or network structure or matrix may be by any suitable means, depending on the nature of the polymer.

The polymer will in general be a hydrophilic polymer. It will be capable of swelling in an aqueous liquid. In one embodiment of the invention, the hydrogel-forming polymer is collagen. In this embodiment, the collagen hydrogel comprises a matrix of collagen fibrils which form a continuous scaffold around an interstitial liquid and the cells. Dissolved collagen may be induced to polymerise/aggregate by the addition of dilute alkali to form a gelled network of cross-linked collagen fibrils. The gelled network of fibrils supports the original volume of the dissolved collagen fibres, retaining the interstitial liquid. General methods for the production of such collagen gels are well known in the art (e.g. WO2006/003442, WO2007/060459 and WO2009/004351).

The collagen which is used in the collagen gel may be any fibril-forming collagen. Examples of fibril-forming collagens are Types I, II, III, V, VI, IX and XI. The gel may comprise all one type of collagen or a mixture of different types of collagen. Preferably, the gel comprises or consists of Type I collagen. In some embodiments of the invention, the gel is formed exclusively or substantially from collagen fibrils, i.e. collagen fibrils are the only or substantially the only polymers in the gel. In other embodiments of the invention, the collagen gel may additionally comprise other naturally-occurring polymers, e.g. silk, fibronectin, elastin, chitin and/or cellulose. Generally, the amounts of the non-collagen naturally-occurring polymers will be less than 5%, preferably less than 4%, 3%, 2% or 1% of the gel (wt/wt). Similar amounts of non-natural polymers may also be present in the gel, e.g. polylactone, polylactide, polyglycone, polycaprolactone and/or phosphate glass.

In some embodiments of the invention, the hydrogel-forming polymer is alginic acid or a alginate salt of a metal ion. Preferably, the metal is a Group 1 metal (e.g. lithium, sodium, or potassium alginate) or a Group 2 metal (e.g. magnesium, calcium, barium or strontium alginate). Preferably, the polymer is sodium alginate or calcium alginate or strontium alginate, most preferably strontium alginate.

One factor which determines alginate gel permeability is the mannuronic (M) and guluronic (G) acid contents of the gel. Gels with a high M:G ratio have a small intrinsic pore size. The M:G ratio may be manipulated to increase the permeability of gels as necessary to improve the viability of encapsulated cells. High M alginates are, however, more biocompatible and clinically useful than high G alginates which tend to form very brittle and viscous gels. In some embodiments, the G content of the alginate gel is 0-30%. In some embodiments, the M content is preferably 30-70%. In some preferred embodiments, the gel is an alginate gel with a M content of 50-70% or 60-70% and the gel additionally comprises or comprised HEC.

In yet other embodiments of the invention, the hydrogel-forming polymer is a cross-linked acrylic acid-based (e.g. polyacrylamide) polymer.

In yet further embodiments, the hydrogel-forming polymer is a cross-linkable cellulose derivative, a hydroxyl ether polymer (e.g. a poloxamer), pectin or a natural gum.

In some embodiments of the invention, the hydrogel is not thermo-reversible at physiological temperatures, i.e. the sol-gel transition of the hydrogel cannot be obtained at a temperature of 0-40° C.

The structure of the hydrogel may be changed by varying the concentration of the hydrogel-forming polymer in the hydrogel. The structure affects the viability of the cells in the hydrogel, the rate of differentiation of the cells as well as affecting the robustness of the gel and its handling properties.

Preferred concentrations of the hydrogel-forming polymer in the hydrogel are 0.2-2.6% (weight of polymer to volume of interstitial liquid), 0.2-0.4%, 0.4-0.5%, 0.5-0.7%, 0.7-1.1%, 1.1-1.3%, 1.3-2.2% and 2.2-2.6%.

In other embodiments, the concentration of the hydrogel-forming polymer in the hydrogel is above 0.25%, 0.3%, 0.4%, 0.5% or 0.6%. In other embodiments, the concentration of the hydrogel-forming polymer in the hydrogel is below 2.4%, 1.5%, 1.4%, 1.3% or 1.2%. In some preferred embodiments, the concentration of the hydrogel-forming polymer in the hydrogel is about 0.3%, about 0.6% or about 1.2%. In some particularly preferred embodiments, the concentration of the hydrogel-forming polymer in the hydrogel is about 1.2%. In some particularly preferred embodiments of the invention, the hydrogel is formed from about 1.2% sodium alginate or from about 1.2% strontium alginate.

It is recognised that mammalian cells are of different sizes. Preferably the pore size is optimised therefore for the type of cells which are entrapped within the hydrogel. In some embodiments of the invention, the hydrogel is obtained or obtainable using a pore size increasing agent. This agent may form an integral part of the hydrogel when in use, or it may be completely, substantially completely or partially removed from the hydrogel prior to use. Preferably, the pore size increasing agent is an agent which produces pores in the range 0.1-3.0 μm, preferably 0.2-3.0 μm, 0.1-1.0 μm or 0.1-0.4 μm.

The internal pore dimensions of the pores within the hydrogels may be measured by chemically dehydrating the hydrogel, exposing the internal surfaces, coating them with gold and then viewing them using a scanning electron microscope.

In some embodiments, the pore size increasing agent is an agent which is soluble in the interstitial liquid and which dissolves out of the hydrogel over the encapsulation period, thus leaving pores of suitable sizes.

In some preferred embodiments, the pore size increasing agent is hydroxyethyl cellulose (HEC). In this embodiment, HEC may be used in the preparation of the hydrogel; it is then completely, substantially completely or partially removed from the hydrogel prior to use. Preferred concentrations of HEC in the hydrogel (during preparation) include 0.5-3.0% HEC, more preferably 1.0-2.5%, and even more preferably 1.2-2.4% HEC. In some preferred embodiments, the concentration of HEC in the hydrogel (during preparation) is about 1.2% or about 2.4%. (Concentrations are given as weight %). The HEC may be suspended in the gels as micelles. Removal of the HEC may be attained by washing the hydrogel in a suitable aqueous solvent or buffer, e.g. tissue culture medium.

A pore size increasing agent could be of low molecular weight or of a polymeric nature. An example of a low molecular weight compound could be sucrose that can be incorporated into a hydrogel in the form of microcrystals and will dissolve over the encapsulation period. Alternatively it could be any water-soluble polymer. The advantage of using water-soluble polymers compared to small molecular weight compounds is their slower dissolution profile allowing better control over the pore size.

In other embodiments of the invention, the pore size increasing agent may be a water-soluble polymer. Examples of suitable polymers include poly(vinylpyrrolidone), polyethyleneglycol, a high molecular weight glucose-based polymer (e.g. dextran, starch, pullulan), and a celluosecellulose-based polymer (e.g. hydroxypropylmethylcellulose, methylcelluose), methylcellulose, hydroxypropylcellulose, carboxymethylcellulose), poly(vinyl alcohol), polyacrylamide, poly(methyl vinyl ether), and block copolymers of polyethylene glycol and polypropylene glycol (e.g. Pluronics).

In some embodiments of the invention, the pore-size increasing agent is gelatin beads.

In some embodiments of the invention, the hydrogel still comprises detectable levels of the pore-size increasing agent, e.g. a water soluble polymer.

In some embodiments of the invention, the gelling of the hydrogel is facilitated using a compound comprising a multivalent metal cation, e.g. using calcium chloride. In particular, calcium chloride (e.g. 50-200 mM calcium chloride, preferably 75-120 mM calcium chloride) may be used to gel alignate hydrogels.

In other embodiments, of the invention, an alternative metal chloride is used, e.g. magnesium or barium or strontium chloride. Alternatively, other multivalent cations may be used, e.g. $La^{3+}$ or $Fe^{3+}$.

In some embodiments of the invention, the gels (preferably alginate gels) additionally comprises $CO_2$. This may aid cell viability after cell storage, particularly after storage under chilled conditions.

The invention further provides a process for preparing a hydrogel, comprising the step of gelling the hydrogel-forming polymer in the presence of a Group 2 metal salt selected from the group consisting of magnesium and strontium salts.

The interstitial liquid may be any liquid in which polymer may be dissolved and in which the polymer may gel. Generally, it will be an aqueous liquid, for example an aqueous buffer or cell culture medium. The liquid may contain an antibiotic. Preferably, the hydrogel is sterile, i.e. aseptic. Preferably, the liquid does not contain animal-derived products, e.g. foetal calf serum or bovine serum albumin.

The hydrogel comprises a plurality of individual cells retained therein. These cells are in general separated or dispersed within the hydrogel, i.e. the cells are not connected in the form of a tissue or organ. Preferably, the cells are primary cells. The cells are live or viable cells or substantially all of the cells are live or viable. In some embodiments of the invention, the cells are all of the same type. For example, they are all brain cells, muscle cells or heart cells. In other embodiments, the cells are all from the same lineage, e.g. all haematopoietic precursor cells. In some embodiments, the cells are stem cells, for example, neural stem cells or embryonic stem cells. Preferably the cells are mammalian cells.

In some preferred embodiments, the cells are adipocytes, astrocytes, blood cells, blood-derived cells, bone marrow cells, bone osteosarcoma cells, brain astrocytoma cells, breast cancer cells, cardiac myocytes, cerebellar granule cells, chondrocytes, corneal cells, dermal papilla cells, embryonal carcinoma cells, embryonic stem cells, embryo kidney cells, endothelial cells, epithelial cells, erythroleukaemic lymphoblasts, fibroblasts, foetal cells, germinal matrix cells, hepatocytes, intestinal cells, keratinocytes, keratocytes, kidney cells, liver cells, lung cells, lymphoblasts, melanocytes, mesangial cells, meningeal cells, mesenchymal stem cells, microglial cells, neural cells, neural stem cells, neuroblastoma cells, oligodendrocytes, oligodendroglioma cells, oral keratinocytes, organ culture cells, osteoblasts, ovarian tumour cells, pancreatic beta cells, pericytes, perineurial cells, root sheath cells, schwann cells, skeletal muscle cells, smooth muscle cells, stellate cells, synoviocytes, thyroid carcinoma cells, villous trophoblast cells, yolk sac carcinoma cells, oocytes, sperm and embryoid bodies. In some embodiments of the invention, the cells are corneal cells.

In other preferred embodiments of the invention, the cells are corneal stem cells preferably comprising limbal epithelial cells, i.e. a heterogeneous mixture of stem cells and differentiated cells which is obtainable from the limbus at the edge of the cornea. In other words, the composition comprising corneal stem cells may comprise a mixture of corneal stem cells and cells that have not yet fully committed to a corneal epithelial phenotype. In other embodiments, the cells include stromal progenitor cells such as corneal fibroblasts (keratocytes) in an differentiated or undifferentiated form. Preferably, these corneal fibroblasts are obtained from the peripheral limbus or from limbal rings which are incubated overnight with about 0.02% collagenase at about 37° C. In another preferred embodiment, the cells are bone marrow cells. In other embodiments, the cells are chondrocytes. In yet other embodiments, the cells are epithelial cells.

As used herein, the term "suppressing or preventing cell division" means that the rate of cell division within all or a substantial proportion of the cells contained within the hydrogel (for a given temperature) is at a lower level than that of control cells which are maintained under appropriate tissue culture conditions at the same given temperature and which are not entrapped or encapsulated in a hydrogel. A substantial proportion may be at least 50%, 60%, 70%, 80%, 90% or 95%.

As used herein, the term "suppressing or preventing cell differentiation" means that the rate of cell differentiation within all or a substantial proportion of the cells contained within the hydrogel (for a given temperature) is at a lower level than that of control cells which are maintained under appropriate tissue culture conditions at the same given temperature and which are not entrapped or encapsulated in a hydrogel. A substantial proportion may be at least 50%, 60%, 70%, 80%, 90% or 95%.

The cells are generally seeded into the hydrogel during the formation of the hydrogel from its constituent polymers, for example, by mixing the cells with a solution of the monomer prior to polymerization/aggregation or prior to cross-linking of a hydrogel-forming polymer.

For this reason, the hydrogel is gelled under appropriate cell-compatible conditions, i.e. conditions which are not detrimental or not significantly detrimental to the viability of the cells.

In some embodiments of the invention, the concentration of cells which are present in the hydrogel is $1\times10^3$-$1\times10^6$ cells/ml hydrogel solution. Generally the concentration of cells is less than $5\times10^5$, preferably $0.1\times10^5$-$5\times10^5$ cells/ml hydrogel, more preferably $0.5\times10^5$-$2.3\times10^5$ cells/ml hydrogel, and most preferably $1.0\times10^5$-$2.0\times10^5$ cells/ml hydrogel. Particularly preferred cell concentrations include:

up to $2.5\times10^5$ cells/ml for alginate gels maintained under cell culture conditions;

up to $1.5\times10^5$ cells/ml for alginate gels maintained under ambient conditions;

up to $1.5\times10^5$ cells/ml for an alginate gel disc maintained under cell culture, chilled or ambient conditions.

In the invention, the cells are embedded in the hydrogel, i.e. the cells are generally entrapped or encapsulated within the hydrogel and not merely placed on a surface of a hydrogel.

The hydrogels may be produced in any suitable size. For ease of transportation, however, the hydrogels are preferably less than 100 mm in length, preferably less than 50 mm in length. The thickness of the hydrogel is generally 0.1-5 mm, preferably 1.0-2.0 mm, more preferably about 1.5 mm.

The volume of the hydrogels of the invention is preferably 0.2-100 ml, more preferably 0.2-50 ml, 0.2-25 ml or 0.2-10 ml. In some preferred embodiments, the volume of the hydrogel of the invention is 0.4-5 ml, preferably 0.4-4 ml, and more preferably 0.4-3 ml. In some embodiments of the invention, the volume may be about 420 µl or about 2 ml.

In some embodiments of the invention, the hydrogel is in the form of a thin layer or disc. The disc may for example, have a diameter of 5-50 mm, preferably 10-30 mm, more preferably 15-25 mm, and most preferably about 19 mm. The thickness of the disc is generally 0.1-5 mm, preferably 0.5-2.0 mm, more preferably about 1.0 or 1.5 mm. In some embodiments, the volume of hydrogel in the disc is preferably 200-600 µl, preferably 300-500 µl and more preferably 400-450 µl.

With regard to the discs of the invention, the preferred hydrogel polymer concentration is about 1.2% due to the increased structural stability provided by this concentration. Preferably, the hydrogel (e.g. a disc) is an uncompressed hydrogel, i.e. it has not been subjected to an axial compressing force.

In some embodiments, the hydrogels are prepared under GMP (Good Manufacturing Practice) conditions.

For transportation or delivery of the cells in the hydrogel, the hydrogel may be appropriately packaged. For example, the hydrogel may be physically protected in order to prevent mechanical damage to the hydrogel. It may also be wrapped, treated or encased in order to prevent water loss.

During transportation and/or storage, the hydrogel comprising cells may be maintained in contact with (e.g. fully or partially immersed in) an appropriate media. Suitable media include cell or tissue culture media, e.g. supplemented DMEM media.

For example, the hydrogel may be enclosed within a water-tight or air-tight material or container, e.g. a plastic container. Alternatively, the hydrogel may be contained within a vial or cryovial or tissue culture flask, optionally together with appropriate media (e.g. cell culture media). In other embodiments, the hydrogel may be contained within a sealed bag, with a controlled $CO_2$ level.

The cells may be transported by any suitable means, e.g. by post or courier, which might include transportation by automotive means, e.g. by car, van, lorry, motorcycle, aeroplane, etc. Preferably, the transportation is by post or courier.

The second location is preferably a location which is remote from the first location, e.g. at least 1 mile, preferably more than 5 miles, from the first location.

In yet a further aspect, the invention provides a method for fulfilling an order or request for cells, the method comprising the steps: (i) receiving an order or request for cells; (ii) encapsulating or entrapping the desired cells in a hydrogel; (iii) dispatching the cell-containing hydrogel for transportation to the location specified in the order or request; and optionally, (iv) transporting the cell-containing hydrogel to the location specified in the order or request.

The order or request may be received by any suitable means, e.g. via the internet, email, text-message, telephone or post.

A particularly preferred embodiment of the invention relates to a 0.6% calcium alginate hydrogel comprising living cells.

A further particularly preferred embodiment of the invention relates to a 1.2% calcium alginate hydrogel comprising living cells, wherein the hydrogel is in the form of a thin layer or thin disc. Such a hydrogel is particularly suitable for maintaining the viability of the cells entrapped therein under ambient storage conditions, preferably epithelial cells.

The invention further provides a process for the preparation of a hydrogel comprising living cells, the process comprising the steps: (i) gelling a hydrogel-forming polymer in the presence of living cells and a water-soluble pore size increasing agent; and (ii) dissolving all or a substantial proportion of the pore size increasing agent out of the hydrogel.

The invention further provides the use a pore size increasing agent in the preparation of a hydrogel. Preferably, the pore size increasing agent is HEC.

Additionally, the invention provides a process for the preparation of a hydrogel comprising living cells, the process comprising the step: (i) gelling a hydrogel-forming polymer in the presence of living cells and of a metal salt selected from the group consisting of magnesium and strontium.

In other embodiments, the invention provides a process for the preparation of a hydrogel comprising living cells, the process comprising the step: (i) gelling a hydrogel-forming polymer in the presence of living cells, wherein the hydrogel is gelled in the form of a thin layer or disc.

The hydrogels may be stored during transportation or otherwise. The hydrogels comprising living cells may be stored at −80° C. to 45° C., preferably at 4 to 45° C. In some embodiments, the hydrogels are stored under cell culture conditions (e.g. about 37° C., about 5% $CO_2$ and about 95% humidity). In some embodiments, the hydrogels of the invention are stored under chilled conditions, e.g. 4-6° C., preferably about 4° C. In other embodiments, the hydrogels of the invention are stored under ambient conditions, e.g. 10-25° C., preferably 18-22° C. In some embodiments, the ambient temperature may be up to 30° C., or even up to 40° C. In yet other embodiments, the hydrogels of the invention are stored at about 37° C.

In some embodiments of the invention, the hydrogel comprising cells is frozen prior to storage and/or transportation. This may extend the time during which the cells are viable post-thawing and/or increase the usable transit-time. Hence the hydrogel may be used in this way as a post-cryoprotectant. For example, the temperature of the hydrogel comprising cells may be reduced to below 0° C., below −15° C. or below −80° C.

The hydrogel comprising cells may or may not be allowed to defrost or thaw, i.e. to increase its temperature to above 0° C. during storage and/or transportation, preferably at a slow, controlled or uncontrolled rate of temperature increase. In other embodiments the hydrogels of the invention are not chilled or frozen.

The hydrogel with living cells retained therein may be stored (e.g. during transportation) for up to 10 or 20 weeks. Preferably, the cells are stored in the hydrogel for up to 1, 2, 3, 4, 5, 6, 7, 8, 9 or 10 weeks before being released from the hydrogels. More preferably, the cells are stored in the hydrogel for up to 1, 2, 3, 4, 5, 6, 7, 8, 9 or 10 days before being released from the hydrogels.

The hydrogel referred to herein is one from which living cells can be released. In other words, after the preservation or storage or transport of the cells contained therein, the hydrogel is capable of being dissociated thus allowing the release or removal of all or substantially all of the cells which were previously retained therein.

The hydrogel is dissociated under appropriate cell-compatible conditions, i.e. conditions which are not detrimental or not significantly detrimental to the cells. Preferably, the hydrogel is dissociated by being chemically disintegrated or dissolved. For example, alginate gels may be disintegrated in an appropriate alginate dissolving buffer (e.g. 0.055 M sodium citrate, 0.15 M NaCl, pH 6.8).

Preferably, at least 50%, 60% or 70% of the cells remain viable after storage, more preferably at least 80%, 85%, 90% or 95% of the cells remain viable after storage. Viability may be assessed by Trypan blue exclusion assay or other similar means. Other similar means include the MTT (3-(4,5-dimethylthiazol-2-yl)-2,5-diphenyltetrazolium bromide) assay and examination of cell colony formation post-extraction.

In other embodiments, the invention provides the use of a hydrogel as described herein as a wound dressing. Thus in a further embodiment of the invention, there is provided a method of treating a wound or an illness caused by a wound in a subject, the method comprising contacting the wound with a hydrogel of the invention. The invention further provides a hydrogel of the invention for use as a wound dressing.

Also provided is the use of a hydrogel of the invention in the manufacture of a medicament for the treatment of wounds or an illness caused by a wound. In some embodiments, the wound may be due to injury (e.g. a burn, abrasion, laceration, or more traumatic injury such as a battlefield injury) or surgery or any other causes.

In a further embodiment, there is provided a method of aiding blood clotting in a subject which is bleeding, the method comprising contacting the site of bleeding with a hydrogel of the invention. The invention further provides a hydrogel of the invention for use as a blood clotting agent.

Also provided is the use of a hydrogel of the invention in the manufacture of a medicament for the treatment of bleeding. The bleeding may be from an external or internal surface or tissue.

In a further embodiment, the invention provides a method of treating an ocular injury in a subject, the method comprising the steps: (a) providing a hydrogel comprising corneal stem cells; (b) contacting the ocular injury with said hydrogel; and optionally (c) securing the said hydrogel at the site of the ocular injury.

Ocular injuries that might be treated include those related to an insufficient stromal micro-environment to support stem cell function, such as aniridia, keratitis, neurotrophic keratopathy and chronic limbitis; or related to external factors that destroy limbal stem cells such as chemical or thermal injuries, Stevens-Johnson syndrome, ocular cicatricial pemphigoid, contact lens wear, or extensive microbial infection.

Preferably, the subject is a mammal, most preferably a human. Suitable hydrogels have been described herein.

The hydrogel comprising corneal stem cells preferably comprises limbal epithelial cells, i.e. a heterogeneous mixture of stem cells and differentiated cells which is obtainable from the limbus at the edge of the cornea. In other words, the hydrogel comprising corneal stem cells may comprise a mixture of corneal stem cells and cells that have not yet fully committed to a corneal epithelial phenotype.

As used herein, the term "corneal" cells refers to cells which have been obtained from an animal (preferably mammalian) cornea. Preferably, the cells are obtained from the limbal ring of the cornea, i.e. the outer edge of the cornea excluding the conjunctiva, iris and central cornea. The cells may comprise or consist of epithelial cells. The cells may comprise or consist of corneal stem cells, preferably limbal corneal epithelial stem cells. Preferably, the corneal stem cells are human corneal stem cells.

The cells are preferably isolated within a GMP facility or surgical theatre. The cells may be obtained from the subject to be treated, from a relative of the subject to be treated or from non-related donor. In some embodiments, the cells may be derived from a non-damaged eye from the subject to be treated.

Preferably, the cells are obtained from the same species as the subject.

The damaged ocular surface may be prepared by removing diseased cells and/or tissue. This may be done using standard surgical procedures, in order to expose the underlying corneal stroma. The hydrogel comprising corneal stem cells may then be placed onto or over the damaged ocular surface, e.g. onto or over the corneal stroma. The hydrogel may be secured in place by appropriate means, e.g. using a therapeutic contact lens or inserting the hydrogel under the conjunctiva (the membrane surrounding the cornea), e.g. by first separating the conjunctiva from the sclera, then pulling the conjunctiva across the cornea and hydrogel gel. An appropriate suture, e.g. a purse string suture, may be used. The conjunctiva is now covering both the hydrogel and the cornea. A therapeutic contact lens might also be used to cover the conjunctiva. Optionally, the eyelid may be sutured closed to prevent infection and/or to maintain the position of the hydrogel, e.g. for 1 to 14 days.

In yet a further embodiment, the invention provides a method of treating a subject having a damaged ocular surface, the method comprising the steps: (a) providing a hydrogel comprising corneal stem cells and/or growth factors secreted or secretable by corneal stem cells; (b) optionally removing diseased cells and/or tissue from the damaged ocular surface of the subject; (c) contacting the damaged ocular surface with said hydrogel; and (d) optionally securing the said hydrogel at the site of the damaged ocular surface.

The invention further provides a method of treating a damaged ocular surface in a subject, the method comprising the steps: (a) providing a hydrogel comprising corneal stem cells and/or growth factors secreted or secretable by corneal stem cells; (b) optionally removing diseased cells and/or tissue from the damaged ocular surface of the subject; (c) contacting the damaged ocular surface with said hydrogel; and (d) optionally securing the said hydrogel at the site of the damaged ocular surface.

As the hydrogel dissolves and/or disaggregates, it will release limbal cell derived growth factors and/or the limbal cells to the damaged ocular surface. Transplanted cells may either directly repopulate the damaged ocular surface or facilitate the recruitment of therapeutically-advantageous host cells to the wound site, thereby regenerating the damaged ocular surface. The hydrogel will be washed away gradually via the tear duct and then excreted via the kidneys, or washed directly away from the surface of the eye by a clinician. Excess transplanted cells may also be removed by similar means after a period of weeks, e.g. 1-4 weeks.

Any of the method of treating steps may be combined with any of the methods of transporting cells, methods of preparing cells, methods of fulfilling an order, methods of suppressing or preventing cell division steps described herein.

For example, the invention provides a method of treating an ocular injury in a subject, the method comprising the steps: (a) encapsulating or entrapping corneal stem cells in a hydrogel; (b) transporting the cell-containing hydrogel from a first location to second location; (c) contacting the ocular injury with said hydrogel; and optionally (d) securing the said hydrogel at the site of the ocular injury.

In addition to the hydrogel, one or more other agents may be applied to the eye, e.g. an antibiotic, an anti-inflammatory agent, etc.

The invention further provides a hydrogel comprising corneal stem cells and/or growth factors secreted or secretable by corneal stem cells for use in therapy or for use as a medicament.

The invention further provides a hydrogel comprising corneal stem cells and/or growth factors secreted or secretable by corneal stem cells for use in treatment of an ocular injury or in treatment of a damaged ocular surface.

The invention further provides the use of a hydrogel comprising corneal stem cells and/or growth factors secreted or secretable by corneal stem cells in the manufacture of a composition or medicament for treatment of an ocular injury or in treatment of a damaged ocular surface.

It will be appreciated that the disclosures herein relating to hydrogels apply, mutatis mutandis, to the methods of treating aspects of this invention. In this context, the hydrogel is preferably a 0.6-2.4% alginate gel, e.g. sodium or calcium or strontium alginate gel, preferably strontium alginate gel, optionally produced using a pore increasing agent (e.g. HEC) as described herein.

Particularly advantageous results have been obtained by using hydrogels in the form of a thin layer or disc or sheet. Hydrogels in such forms are shown herein to enhance the viability of cells. The thin layer or disc or sheet is preferably isolated.

Preferably, the gel is in the form of a disc or thin layer. The diameter of the disc is preferably 10-50 mm. The final volume of the gel is preferably 1-5 ml. The thickness of the thin layer or disc or sheet is preferably 0.1-5 mm, e.g. about 1, 2, 3, 4 or 5 mm.

In yet a further embodiment, the invention provides a kit for producing a hydrogel comprising living cells, the kit comprising: (a) a hydrogel-forming polymer; and (b) a population of living cells. Additionally, the kit may comprise one or more of the following: (c) an interstitial liquid; (d) a pore-size increasing agent, preferably a water-soluble pore-size increasing agent; (e) a mould for forming a gel; (f) instructions for the preparation of a hydrogel comprising living cells; (g) packaging to prevent mechanical damage to the hydrogel; (h) an address label.

In some particularly preferred embodiments of the invention, the hydrogel comprises 1.2% alginate and the pore size increasing agent is 1.2% HEC; and such gels are stored at ambient temperature.

It has been found that the mechanical strength of the hydrogel may be enhanced by the encapsulation of a reinforcing structure, scaffold or mesh within the gel. It may be synthetic or natural polymer. Preferably, the reinforcing structure, scaffold or mesh is biodegradable. The reinforcing structure, scaffold or mesh may, for example be a polymer comprising polylactic acid (e.g. poly(lactic acid-co-caprolactone) (PLACL)), collagen or nylon.

In yet other embodiments of the invention, the hydrogel comprises a nylon mesh. Such a composite material has the advantage of being more robust than an alginate gel and less likely to break up during storage or transit of the gel. A further benefit is that the nylon mesh may be sutured, thereby allowing the gel to be held by stitches. The nylon mesh may be within the gel, partially within and partially outside the gel or outside (i.e. on a surface of) the gel. The nylon mesh preferably has a mesh size of 0.01-100 μm. Preferably, it is made of a suitable non-toxic material, which may be soluble or insoluble.

In a preferred embodiment, the hydrogel is in the form of a disc comprising a nylon mesh. Preferably, the nylon mesh is embedded within the disc.

EXAMPLES

Figure 1:
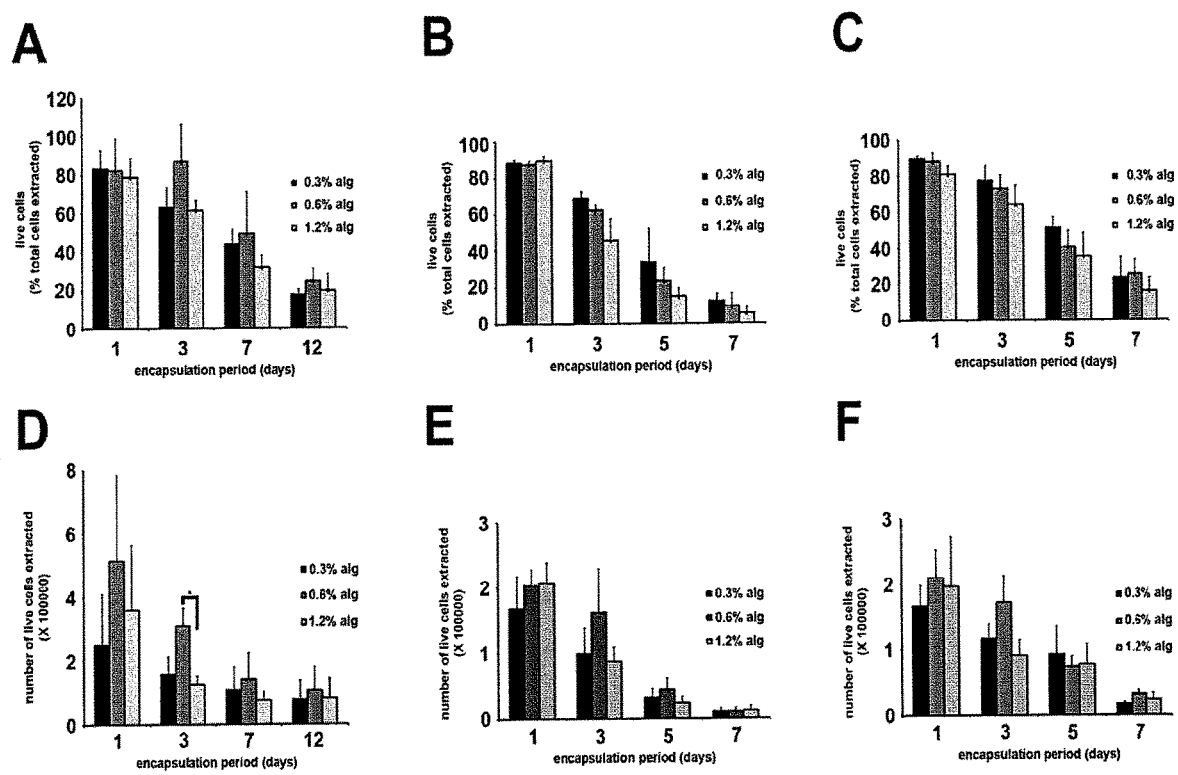
FIG. 1. The viability of a corneal epithelial cell-line in calcium alginate gel masses is dependent on polymer concentration, period of encapsulation and storage condition. HCE cells extracted from 0.3%, 0.6% and 1.2% calcium alginate gel masses maintained for 1, 3, 5, 7 and/or 12 days under cell culture (A, D), ambient (B, E) and chilled (C, F) conditions were washed and suspended in medium. Numbers of live and dead cells were assessed by Trypan blue exclusion. Proportions of live cells were expressed as a percentage of total cells (100%) extracted from gels. Data points represent the mean (n=3) percentage live cells extracted. * P≤0.05 indicate differences between alginate concentrations.

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Materials and Methods
Culture of a Human Corneal Epithelial (HCE) Cell-Line

A human corneal epithelial (HCE) cell-line was cultured in Dulbecco's minimal essential medium (DMEM) and Ham's F12 medium (DMEM/F12, 1:1), supplemented with 10% fetal bovine serum (FBS: Hyclone, UK), 0.5% dimethylsulphoxide (DMSO: Sigma-Aldrich, Poole, UK), 10 ng/ml human epidermal growth factor (hEGF: Sigma-Aldrich, Poole, UK), 5 mg/nil insulin (Sigma-Aldrich, Poole, UK), 100 IU/ml penicillin and 100 mg/ml streptomycin at 37° C. under 5% $CO_2$ and 95% humidity. Cells were replenished with fresh medium every 3 days and grown to 70-80% confluency.

Isolation of Epithelial Cells from the Cornea

The established bovine cornea model (20-21) was used for the isolation of limbal epithelial cells. Normal bovine eyes were obtained from a local abattoir (Chity whole sale abattoir, Guildford, UK) within 2 h of death, transported to the laboratory at 4° C. and used immediately. Corneoscleral buttons were dissected using standard eye bank techniques, as previously described (22).

Encapsulation of Epithelial Cells in Calcium Alginate Gel Masses and Discs

HCE and limbal epithelial cells were suspended in 0.3%, 0.6% and/or 1.2% (w/v) sodium alginate solutions before gelling into masses and discs using 102 mM $CaCl_2$, as described previously (23). Gel masses and discs were formed by pipetting 2 mL sodium alginate/cell solutions into 102 mM $CaCl_2$ and using chromatography paper molds (Whatman) immersed in 102 mM $CaCl_2$ respectively.

Calcium alginate gel masses and discs were suspended in supplemented DMEM/F12 medium under cell culture (37° C., 5% $CO_2$, 95% humidity), ambient (18-22° C., atmospheric $CO_2$ and humidity levels) and chilled (4° C., atmospheric $CO_2$ and humidity levels) conditions, for 1, 3, 5, 7 and/or 12 days. Under cell culture storage, gels were seeded with $5 \times 10^5$ cells/2 mL gel. Initial experiments performed under ambient and chilled conditions using gels seeded with $5 \times 10^5$ cells/2 mL gel, demonstrated a rapid decline in cell viability, that was prevented by reducing cell numbers to $3 \times 10^5$ cells/2 mL gel; periods of encapsulation were restricted to 7 days as cells did not remain alive for longer periods of time. Gel/cell matrices were replenished with fresh medium every 2 days. Loss of cells from calcium alginate gel masses due to the extraction process was minimal.

Cell Viability Analysis

Cells were extracted from calcium alginate gel masses and discs using alginate dissolving buffer (0.15 M NaCl, 0.055 M sodium citrate). Cells from individual conditions were cultured in supplemented DMEM/F12 for approximately 3 days for HCE and 2 weeks for limbal epithelial cells to monitor the ability of these cells to attach and form colonies post-extraction. Images of cell colonies were obtained at 100× magnification.

The Trypan blue exclusion assay was performed by mixing a 10 μL cell suspension with 10 μL Trypan blue dye solution (v/v), before counting live (unstained) and dead (stained-blue) cells using a haemocytometer. The MTT (3-(4,5-dimethylthiazol-2-yl)-2,5-diphenyltetrazolium bromide) assay was performed to assess cell metabolic activity, following the manufacturer's protocols. Briefly, 12 mM 3-(4,5-dimethylthiazol-2-yl)-2,5-diphenyltetrazolium bromide was added to a 100 μL suspension of cells and this was incubated for 2 h at 37° C. Cells were then lysed using dimethylsulphoxide (DMSO), incubated for a further 10 min at 37° C., mixed and the absorbance of the reaction product (formazan) was measured at 540 nm.

Scanning Electron Microscopy (SEM) Analysis of Calcium Alginate Structure

The internal surfaces of 0.3%, 0.6% and 1.2% calcium alginate gels were examined by SEM. Gels were fixed in 1.25% (v/v) glutaraldehyde and post-fixed for 2 hours in 1% aqueous osmium tetroxide, washed in distilled water and passed through a graded ethanol series (50%, 70%, 90% and 100%) before dehydration through critical point drying. Dehydrated gels were mounted on aluminium stubs and sputter coated with gold before examination using SEM (FEI Quanta FEG 600, UK).

Statistical Analysis

Unpaired Student's t-tests were performed using Microsoft Excel. Results are presented as the mean of 3 individual experiments with standard error of mean and P-value≤0.05 considered significant.

Results
Calcium Alginate Supports Corneal Epithelial Cell Viability in a Differential Manner Under Various Storage Conditions The ability of a calcium alginate gel to support viable corneal epithelial cells was investigated to examine the suitability of this gel scaffold for the preservation of live cells intended for therapeutic purposes. Immortalised human corneal epithelial (HCE) cells 5, 7 and/or 12 days and stored under cell culture (37° C., 5% $CO_2$, 95% humidity), ambient (18-22° C., atmospheric $CO_2$ and humidity levels) and chilled (4° C., atmospheric $CO_2$ and humidity levels) conditions.

Cell viability was assessed by the Trypan blue exclusion assay and cell attachment and colony formation post-extraction. Proportions of live and dead cells measured using the Trypan blue exclusion assay were expressed as percentages of the total number of cells (100%) extracted from gels.

Figure 2:
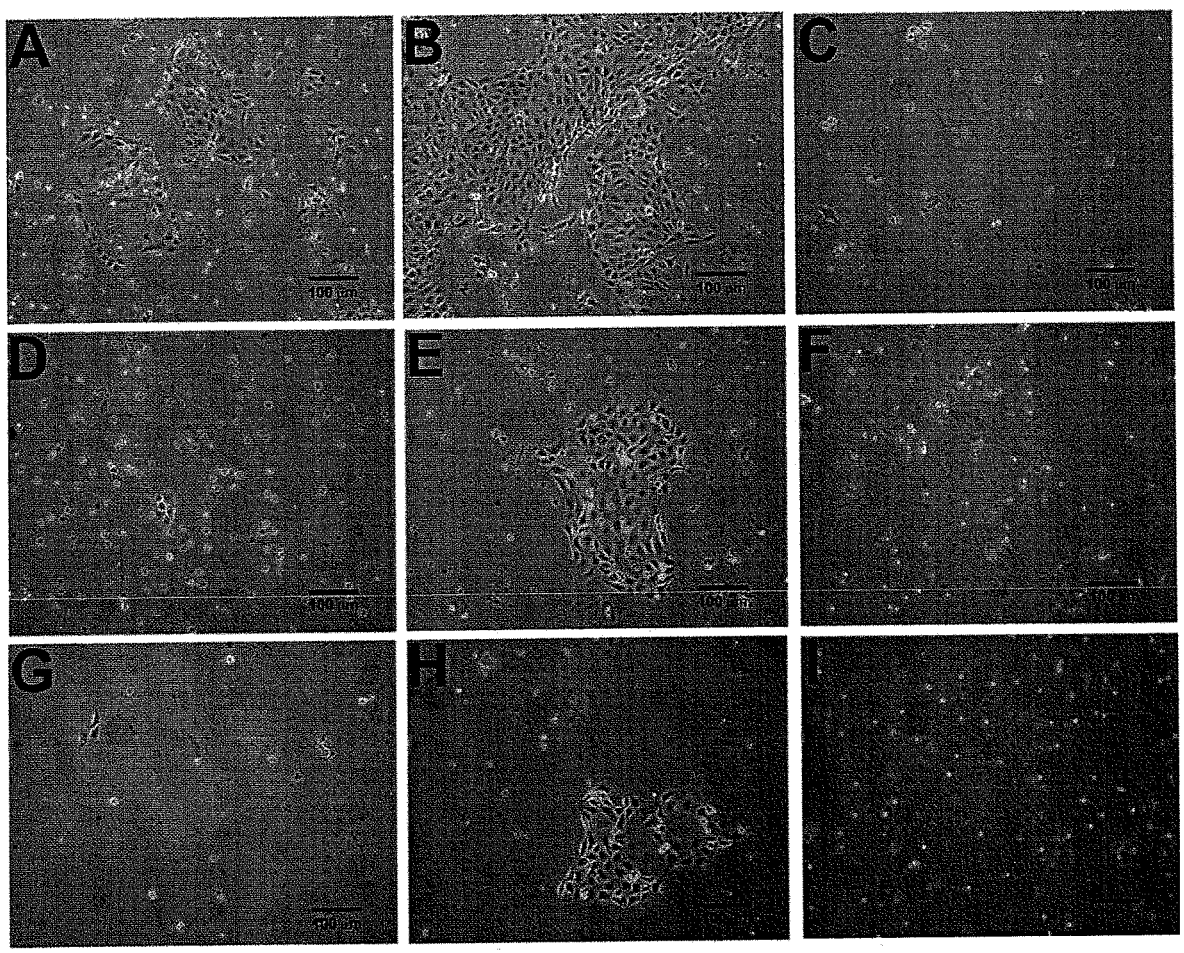
FIG. 2. Corneal epithelial cells extracted from calcium alginate gel masses are able to adhere and assemble into colonies. HCE cells extracted from calcium alginate gel masses maintained for 7 days under cell culture (alginate concentrations—0.3%: A, 0.6%: B, 1.2%: C) and 5 days under ambient (alginate concentrations—0.3%: D, 0.6%: E, 1.2%: F) and chilled (alginate concentrations—0.3%: G, 0.6%: H, 1.2%: I) conditions were washed and suspended in medium. Cells were cultured at 37° C. under 5% $CO_2$ and 95% humidity. Images of cell colonies (100× magnification) represent 3 individual experiments.
Figure 3:
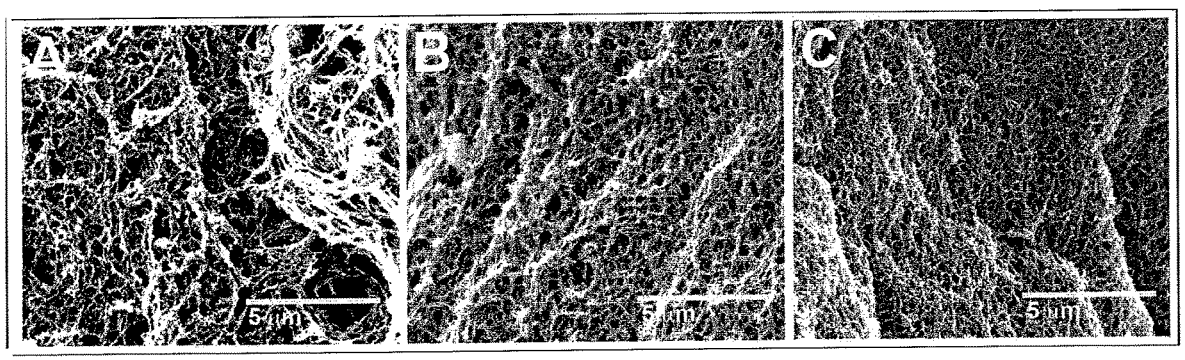
FIG. 3. SEM microphotographs of calcium alginate gels. Calcium alginate gel masses (0.3%: A, 0.6%: B and 1.2%: C) were dehydrated and internal surfaces were examined using SEM. Electron micrographs (19000× magnification) represent 3 individual experiments.

The viability of corneal epithelial cells within calcium alginate was influenced by polymer concentration, period of encapsulation and storage condition (FIG. 1). Cell viability decreased with increased periods of encapsulation under all storage conditions investigated. Similar proportions of viable cells were recovered from calcium alginate gels maintained under cell culture (32-49%) and chilled (35-51%) conditions over 7 and days respectively (compare FIGS. 1A and 1C), but cells from cell culture storage assembled into larger colonies (FIG. 2A-2C) than those from ambient (FIG. 2D-2F) or chilled (FIG. 2G-2I) storage.

Gels comprising 0.3% or 0.6% alginate supported greater levels of viable cells than 1.2% alginate gels under cell culture (FIGS. 1A and 1D), ambient (FIGS. 1B and 1E) and chilled (FIGS. 1C and 1F) storage. Although live cells extracted from both 0.3% and 0.6% alginate gels were able to adhere and assemble into colonies, cells recovered from 0.6% alginate gels (FIG. 2B) formed larger colonies than those from 0.3% alginate gels (FIG. 2A). This pattern of growth was particularly apparent under ambient (FIG. 2D-F) and chilled (FIG. 2G-I) conditions.

The numbers of cells recovered from 0.3% alginate gels were consistently lower than those extracted from 0.6% alginate gels under cell culture storage (FIG. 1D), possibly due to loss of cells from the loose structure (data not shown) of 0.3% alginate gels. The reduction in cell viability in 1.2% alginate gels, however, may be due to detrimental effects of the increased alginate concentration within this gel matrix, as a 0.6% alginate gel retained a significantly greater ($P \leq 0.05$) number of live cells than a 1.2% alginate gel (FIG. 1D). Dead or apoptotic cells may have contributed to the reduction in cell viability and recovery, as the phagocytic cells necessary for their clearance (24-25) were not incorporated within gels.

Taken together, these data demonstrated that a 0.6% alginate gel mass was more suitable for maintaining viable epithelial cells than gel masses containing 0.3% and 1.2% alginate, under cell culture, ambient or chilled storage conditions.

Example 2: The Structure of Calcium Alginate Gels May Influence the Viability of Encapsulated Cells As corneal epithelial cell viability varied within different concentrations of calcium alginate, potential links between the structure of this gel and its ability to support viable cells were investigated. Calcium alginate gel masses (0.3%, 0.6% and 1.2%) were chemically dehydrated and internal surfaces were exposed and coated with gold, before analysis of their morphology using scanning electron microscopy (SEM).

Figure 4:
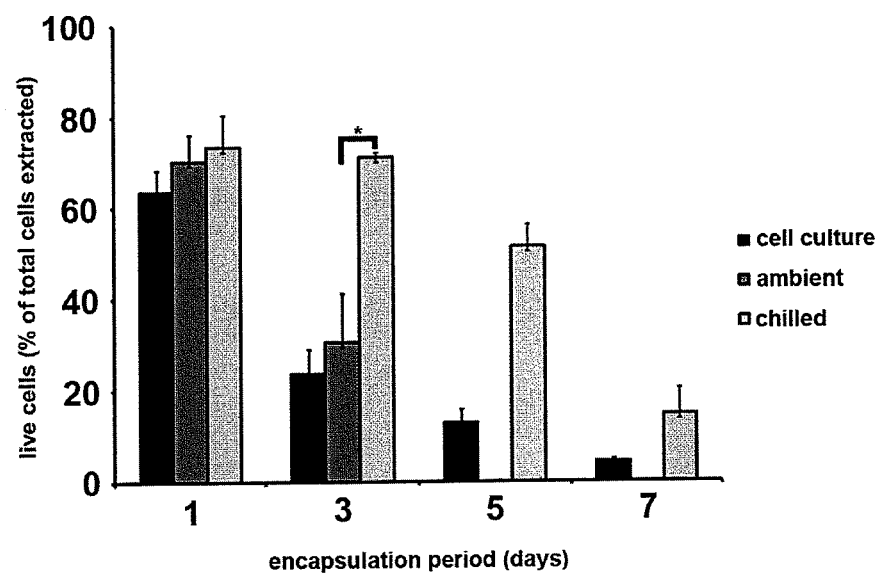
FIG. 4. The viability of limbal epithelial cells within calcium alginate gel masses is influenced by storage conditions. Limbal epithelial cells extracted from 0.6% calcium alginate gel masses maintained for 1, 3, 5 and 7 days under cell culture, ambient or chilled conditions were washed and resuspended in medium. Numbers of live and dead cells were assessed by Trypan blue exclusion. Proportions of live cells were expressed as a percentage of total cells (100%) extracted from gels. Data points represent the mean (n=3) percentage live cells extracted. * P≤0.05 indicate differences between storage conditions.
Figure 4:
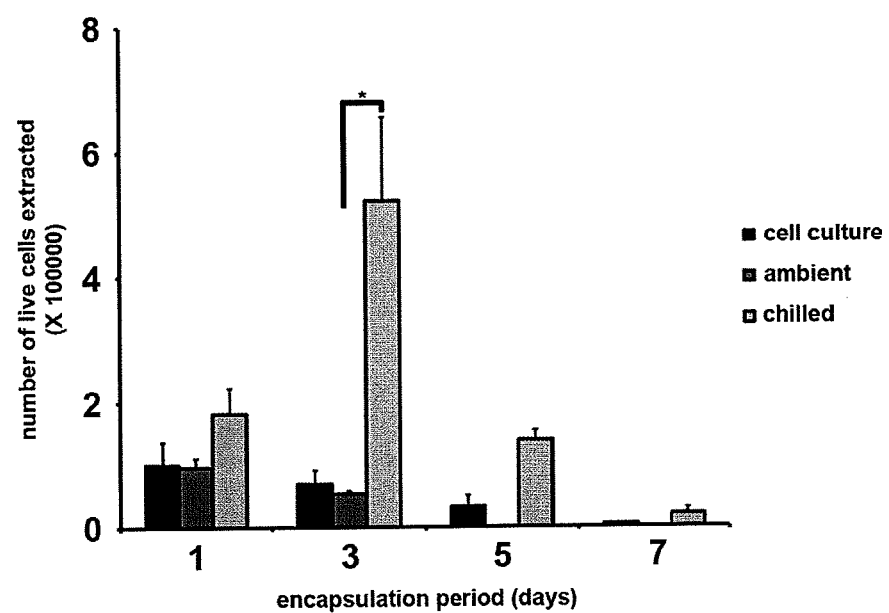

The internal structure of calcium alginate gel masses comprised of irregular pore spaces with dimensions which increased with decreases in alginate concentration (FIG. 4). Pore diameters ranged from 0.2-3.0 µm within a 0.3% alginate gel (FIG. 4A), 0.1-1.0 µm within a 0.6% alginate gel (FIG. 4B) and 0.1-0.4 µm within a 1.2% alginate gel (FIG. 4C). Previous reports showed that solutes migrated at a slower rate through a 3% alginate gel with small pores than through a 1.5% alginate gel with relatively larger pores (6). Therefore, the greater viability of cells in 0.3% and 0.6% alginate gels than 1.2% gels may potentially be due to their more ready access to medium nutrients moving more efficiently through pore spaces which are larger than those within 1.2% alginate gels.

Example 3: Limbal Epithelial Cell Viability in Calcium Alginate Gel Masses is Affected by Storage Conditions To understand the extent of corneal epithelial cell viability within calcium alginate gels in a potentially therapeutic context, epithelial cells isolated from the corneal limbus (bovine model) were encapsulated within this gel. Cells were encapsulated in 0.6% calcium alginate, as this concentration of the gel supported viability more robustly than gels containing 0.3% or 1.2% alginate (see FIGS. 1 and 2). Cell viability was examined over 1, 3, 5, and 7 days under cell culture, ambient and chilled storage conditions by the Trypan blue exclusion assay and cell colony/sheet formation post-extraction.

Figure 5:
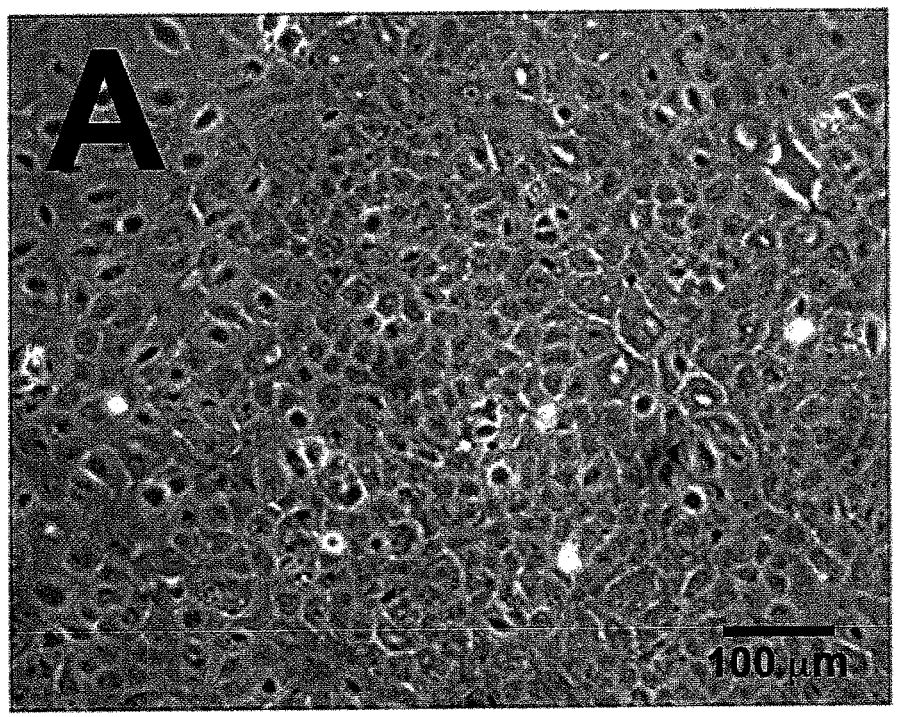
FIG. 5. Limbal corneal epithelial cells extracted from calcium alginate gel masses are able to adhere and assemble into colonies. Limbal epithelial cells extracted from 0.6% calcium alginate gel masses maintained for 5 days under cell culture (A) and chilled (B) conditions, were washed and resuspended in medium. Cells from individual conditions were cultured in supplemented medium 37° C. under 5% $CO_2$ and 95% humidity. Images of cell colonies (100× magnification) represent 3 individual experiments.
Figure 5:
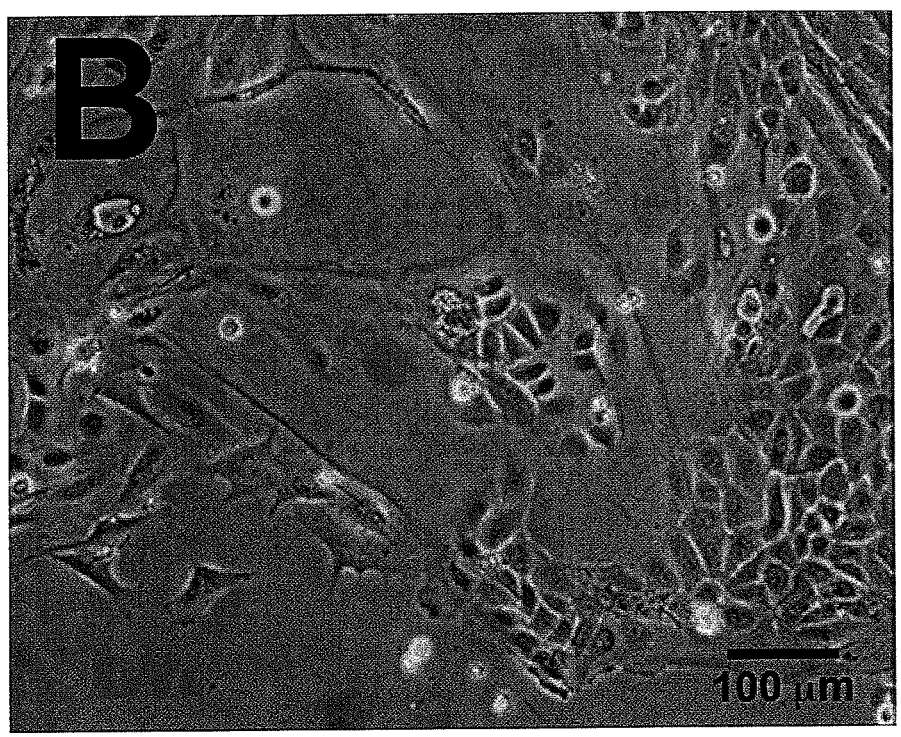

Limbal epithelial cell viability was supported most robustly under chilled and cell culture conditions in 0.6% alginate gel masses. After 1, 3, 5 and 7 day encapsulation periods, 10%, 50%, 35% and 5% more live cells respectively were extracted from calcium alginate gels under chilled conditions than from those stored under cell culture conditions. Post-extraction, however, cells from cell culture storage formed large sheets whereas those from chilled storage only assembled into small colonies (FIG. 5), possibly indicating that live cells from chilled storage were too damaged to adhere.

Under ambient storage, limbal epithelial cell viability was very poor; cells did not remain alive for longer than 3 days (FIG. 4).

Figure 6:
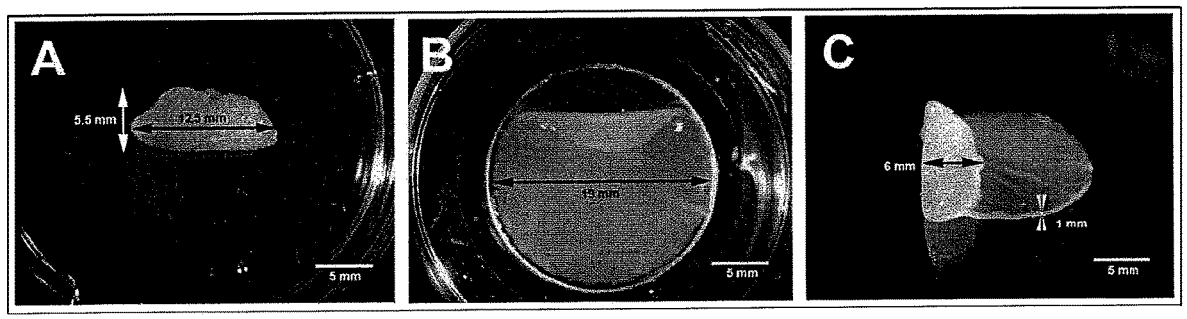
FIG. 6. Calcium alginate gel masses and discs. Calcium alginate was prepared into 0.6% gel masses (A, C) and 1.2% gel discs (B, C). Gel masses were approximately 12.5 mm in length (A) and 6 mm in depth (C), whereas gel discs were approximately 19 mm in length (B) and 1.5 mm in depth (C). Images (100× magnification) represent 3 individual experiments.

Example 4: The Viability of Limbal Epithelial Cells is Enhanced in Thin Discs of Calcium Alginate The effect of gel shape (thickness) on recovery of live limbal epithelial cells was examined. The gel was modified from an amorphous mass (approximately 6 mm depth and 12.5 mm width) to a thin disc (approximately 1.5 mm depth and 19 mm width) that presented a shorter distance (FIG. 6) for movement of medium nutrients to, and waste products from encapsulated cells.

A 1.2% alginate gel that formed structurally more stable discs than 0.3% and 0.6% alginate gels was used, despite the lower levels of viability achieved using this concentration of the gel (see FIG. 1), as it was hypothesised that the reduced depth of the gel would compensate for low cell viability. Cell viability was assessed using the Trypan blue exclusion assay and by examining cell colony/sheet formation post-extraction. To determine whether the difference in limbal epithelial cell attachment and colony formation between cell culture and chilled storage cells (see FIG. 5) was due to differences in levels of active live cells, the MTT assay was used to measure cell metabolic activity.

Figure 7:
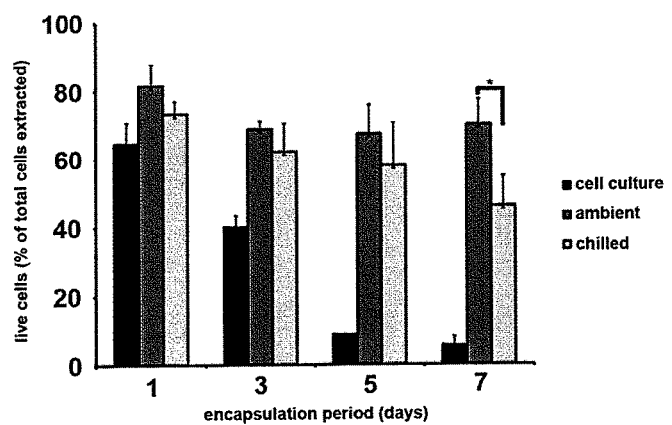
FIG. 7. Limbal epithelial cell viability is enhanced within a thin disc of calcium alginate gel. Limbal epithelial cells extracted from 1.2% calcium alginate gel discs maintained for 1, 3, 5 and 7 days under cell culture, ambient or chilled conditions, were washed and resuspended in medium. Levels of viable cells were measured using Trypan blue exclusion assay (A, B) and functional cells were assessed using the MTT assay (C). Proportions of live cells were expressed as a percentage of total cells (100%) extracted from gels (A). Data points represent the mean (n=3) percentage live cells extracted. * P≤0.05 indicate differences between storage conditions.
Figure 7:
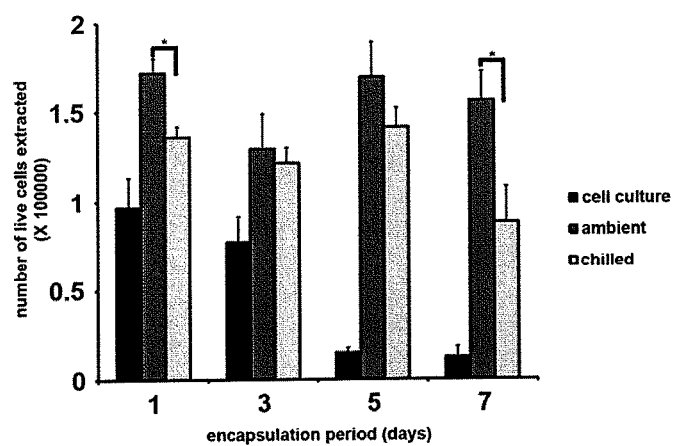
Figure 7:
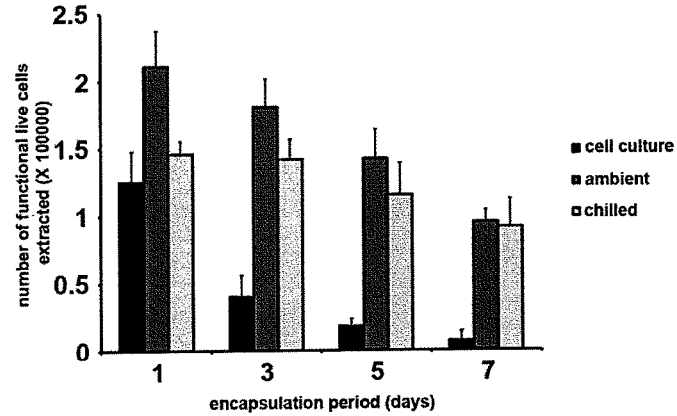

Limbal epithelial cell viability was enhanced in calcium alginate gel discs compared to calcium alginate gel masses, as ambient storage that was demonstrated previously as unable to support viable cells for longer than 3 days in gel masses (see FIG. 4), supported greater levels of viable cells in discs over 1-7 days than cell culture and chilled storage (FIG. 7). Under ambient storage, approximately 65-80% of extracted cells were alive during 1-7 days of encapsulation in alginate gel discs, and at least 70±7% of the total number of encapsulated cells ($3 \times 10^5$) in these gels remained alive after 7 days (FIG. 7A). Proportions and numbers of live cells extracted from gel discs maintained under ambient storage over 1 and 7 days were significantly greater ($P \leq 0.05$) than those extracted from gel discs under chilled storage (FIGS. 7A and 7B).

Figure 8:
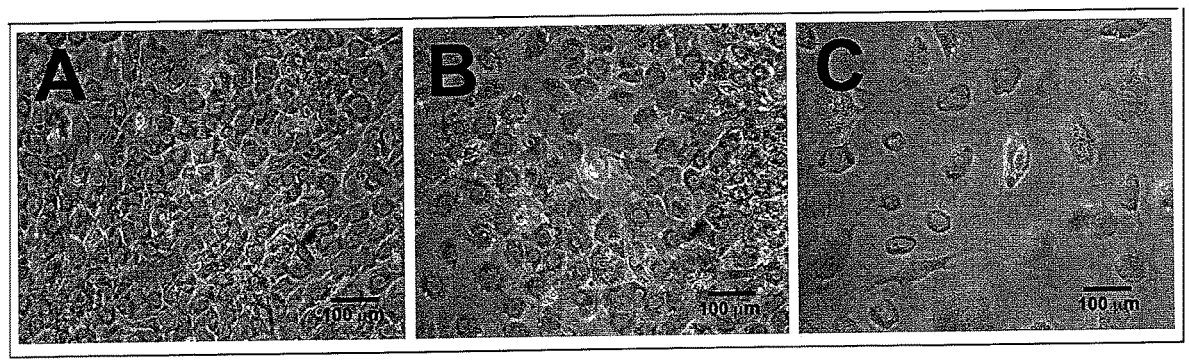
FIG. 8. Limbal epithelial cells extracted from calcium alginate gel discs are able to adhere and assemble into colonies. Limbal epithelial cells extracted from 1.2% calcium alginate gel discs maintained for 7 days under cell culture (A), ambient (B) and chilled (C) conditions, were washed and resuspended in medium. Cells were added to supplemented medium and cultured at 37° C. under 5% $CO_2$ and 95% humidity. Images of cell colonies (100× magnification) represent 3 individual experiments.

As observed within alginate gel masses (see FIG. 4), the lowest levels of viable cells were extracted from gels maintained under cell culture conditions (FIGS. 7A and 7B). Live cells extracted from cell culture storage gel discs were, however, able to assemble into cell sheets (FIG. 8A) similar to live cells extracted from gel discs maintained under ambient storage (FIG. 8B). Only single cells from chilled storage gel discs adhered (FIG. 8C), and the numbers of live metabolically active (FIG. 7C) and total live (FIG. 7B) cells from chilled storage were similar. Therefore, the inability of chilled storage live cells to assemble into colonies or sheets was not due to reduced levels of metabolically active cells.

Collectively, these data demonstrated that modification of the macro-structure of a calcium alginate gel from an amorphous mass to a thin disc enhanced limbal epithelial cell viability, and overcame the reduction in cell viability observed with increases in alginate concentration.

Example 5: Gels Modified Using HEC

To improve the ability of a $Ca^{2+}$ alginate hydrogel to support viable encapsulated cells, a gel was made as described above but modified through the addition of hydroxyethyl cellulose (HEC).

Figure 9A:
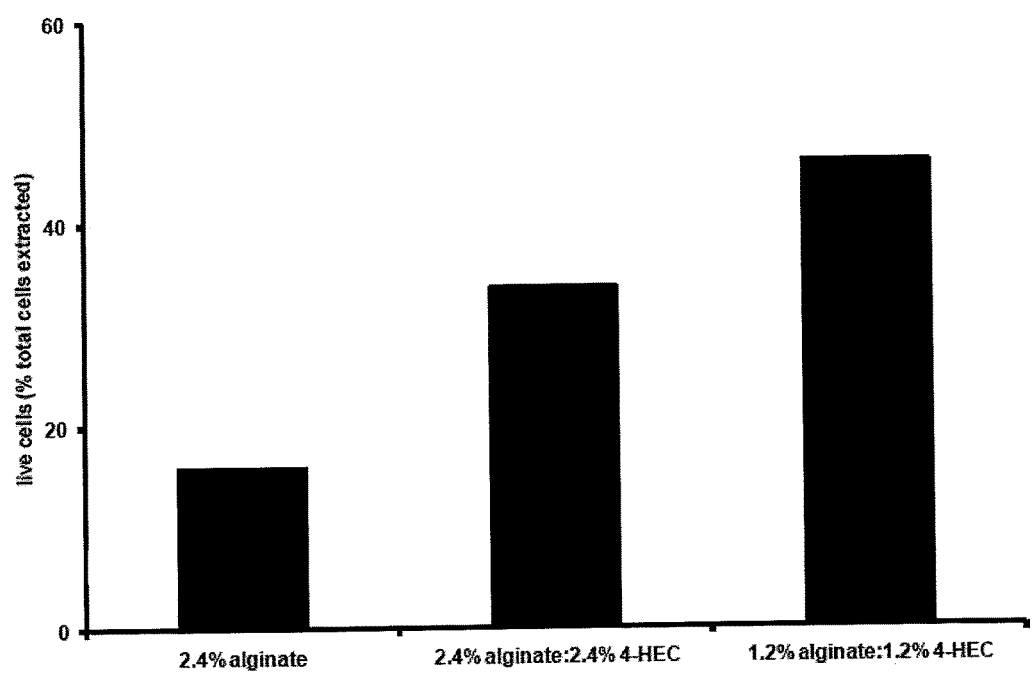
FIG. 9A-B. Corneal epithelial cell viability is enhanced within calcium alginate gels modified with HEC. A: Corneal epithelial cells extracted from 2.4% calcium alginate discs, 1.2% alginate:1.2% HEC discs and 2.4% alginate:2.4% HEC discs maintained for 3 days under cell culture conditions, were washed and resuspended in medium. Levels of viable cells were measured using Trypan blue exclusion assay. Proportions of live cells were expressed as a percentage of total cells (100%) extracted from gels. Data points represent the mean (n=2) percentage live cells extracted. B: 1.2% alginate, 1.2% alginate:1.2% HEC and 1.2% alginate: 2.4% HEC gels were similarly compared.
Figure 9B:
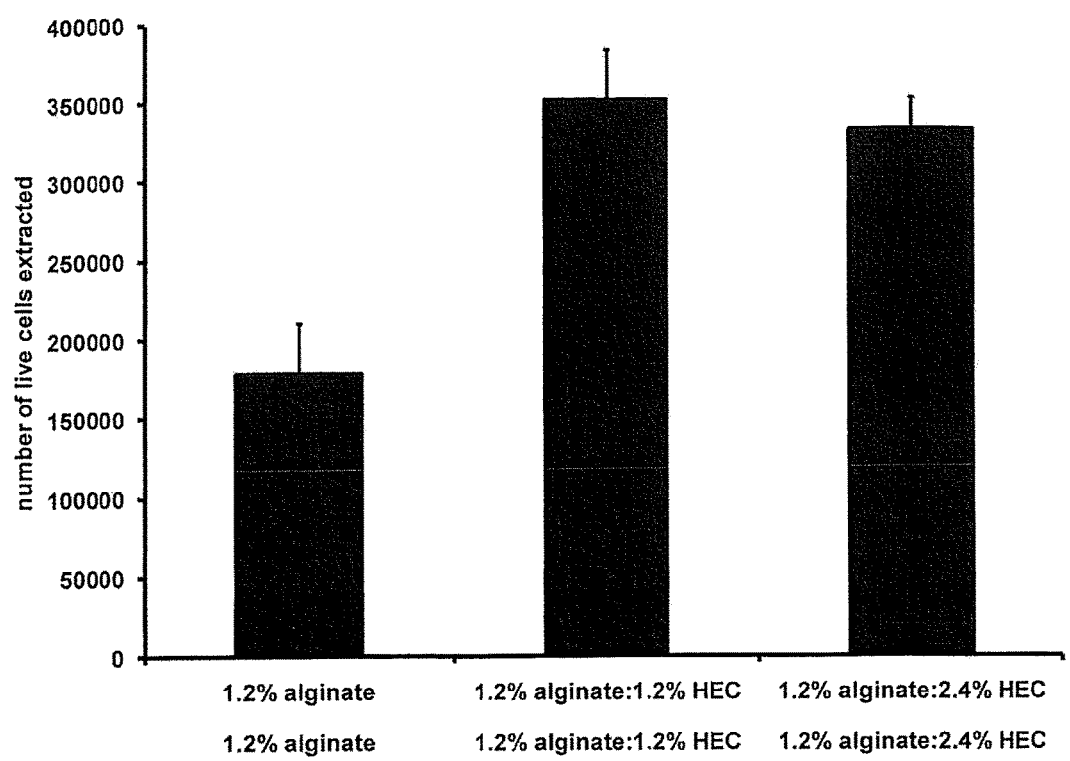

A 2.4% alginate gel containing 2.4% HEC supported 50% greater levels of live cells than a gel containing 2.4% alginate alone (FIG. 9A). Cell viability was enhanced in a 1.2% alginate:1.2% HEC gel compared to a 2.4% alginate: 2.4% HEC gel (FIG. 9). A 1.2% gel supported lower proportions of viable cells compared to a 1.2% alginate: 1.2% HEC gel (FIG. 9B).

Figure 10:
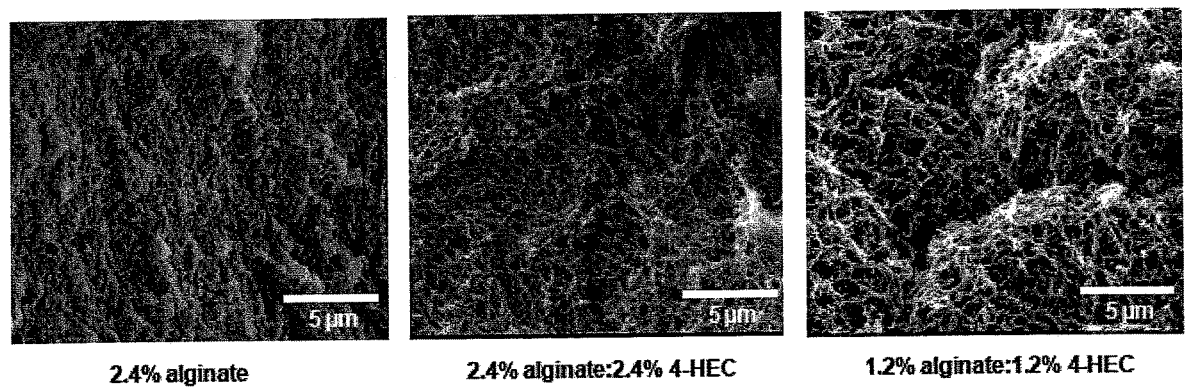
FIG. 10. SEM microphotographs of calcium alginate and calcium alginate/HEC gels. Calcium alginate gel discs were dehydrated and internal surfaces were examined using SEM. Electron micrographs (19000× magnification) represent 3 individual experiments. The references in FIGS. 9A and 10 to "4-HEC" refer to HEC.

The sizes of pore spaces correlated with cell viability (FIG. 10). Greater levels of viable cells were retrieved from gels with large internal pores than from those with relatively smaller internal pores (compare 2.4% alginate with 2.4% alginate:2.4% HEC and compare 2.4% alginate:2.4% HEC with 1.2% alginate:1.2% HEC).

Example 6: Use of Hydrogels as Carriers for Cell Transplantation

Isolation of Limbal Stem Cells
Isolation occurs within a GMP facility or surgical theatre. Tissue pieces approximately 10 mm×5 mm×1 mm in size containing epithelial cells (a proportion of which will be adult stem cells) and underlying stroma from the limbus (the anatomical region of the eye between the white sclera and transparent cornea) is surgically removed by scissors or blade from either donor or contralateral eye. The epithelial cells are dissociated from the tissue using a combination of agitation and enzyme digestion (enzymes include collagenase, dispase, trypsin/EDTA, liberase) for a period between 10 mins and 2 hours at 37° C. in basal culture medium. After this time, the epithelial cells are separated from the rest of the tissue, thereby creating a suspension of limbal epithelial cells containing stem cells.
Encapsulation of Isolated Cells
The number of isolated viable cells is quantified using an automated cell counter. A known number of limbal cells ($1 \times 10^3$ to $1 \times 10^6$ cells/1 mL of sodium alginate solution) is encapsulated in calcium alginate gels. Gels are formed in discs by the addition of calcium chloride to 0.6-2.4% sodium alginate containing or not containing HEC using circular moulds with a diameter of 1-5 cm. The final volume of the gel is 1-5 ml with a thickness of 0.1-5 mm.
Transplantation of Encapsulated Limbal Epithelial Cells
The damaged ocular surface is first prepared by removing diseased cells and tissue using standard surgical procedures to expose the underlying corneal stroma. A disc of calcium alginate gel containing limbal epithelial cells is placed on to the corneal stroma and held in place by either a therapeutic contact lens or inserting under the conjunctiva (membrane surrounding the cornea) by first separating the conjunctiva from the sclera, then the conjunctiva is pulled across the cornea and alginate gel using a purse string suture. The conjunctiva is now covering both the alginate gel and the cornea. A therapeutic contact lens might also cover the conjunctiva. Finally the eyelid may be sutured closed to prevent infection and to maintain the position of the alginate gel.
Therapeutic Effect
As the alginate gel dissolves/disaggregates it will release limbal cell derived growth factors and/or the limbal cells to the damaged ocular surface. Transplanted cells will either directly repopulate the damaged ocular surface or facilitate the recruitment of therapeutically-advantageous host cells to the wound site, thereby regenerating the damaged ocular surface.

The alginate gel will be washed away gradually via the tear duct and then excreted via the kidneys, or washed directly away from the surface of the eye by a clinician. Excess transplanted cells will also be removed by similar means after a period of 1-4 weeks.

Example 7: Determination of M/G Ratios of Alginate Gels

Alginate solution was prepared in deionised water at a concentration of 2.5% (w/v). Alginate solutions (5 cm$^3$ aliquots) were placed in 10 cm$^3$ glass microwave tubes (CEM) and subjected to microwave irradiation using a power input of 200 W, a nominal temperature of 120° C. and a hold time of 5 minutes. This method was adapted from the microwave-assisted rapid hydrolysis method of Chhatbar et al. (Chhatbar M., et al. "Microwave assisted rapid method for hydrolysis of sodium alginate for M/G ratio determination". Carbohydr. Polym. 2009; 76: 650-656), by using a research microwave reactor (CEM Discover LabMate) instead of a domestic microwave oven. The safety cut-off pressure of 200 psi was never reached. Following hydrolysis, the M/G ratio was determined with reference to the method of Chandia et al. (Chandia N P, et al. "Alginic acids in Lessonia trabeculata: characterization by formic acid hydrolysis and FT-IR spectroscopy". Carbohydr. Polym. 2001; 46: 81-87). Briefly, the hydrolysed solution was adjusted to pH 2.85 (monitored with a Mettler Toledo SevenEasy pH meter S20) using 0.1 M HCl (Fisher) solution and the resulting precipitate, poly(guluronic acid) was collected by centrifugation (Denley BS400) and weighed. The supernatant was adjusted to pH 1.0 using 0.1 M HCl solution and the second precipitate, poly(mannuronic acid) was collected by centrifugation and weighed.

The value obtained for the M/G ratio was 3.3±0.3 (77% M/23% G), consistent with the manufacturer's assertion that this alginate has a high M content.

Figure 11:
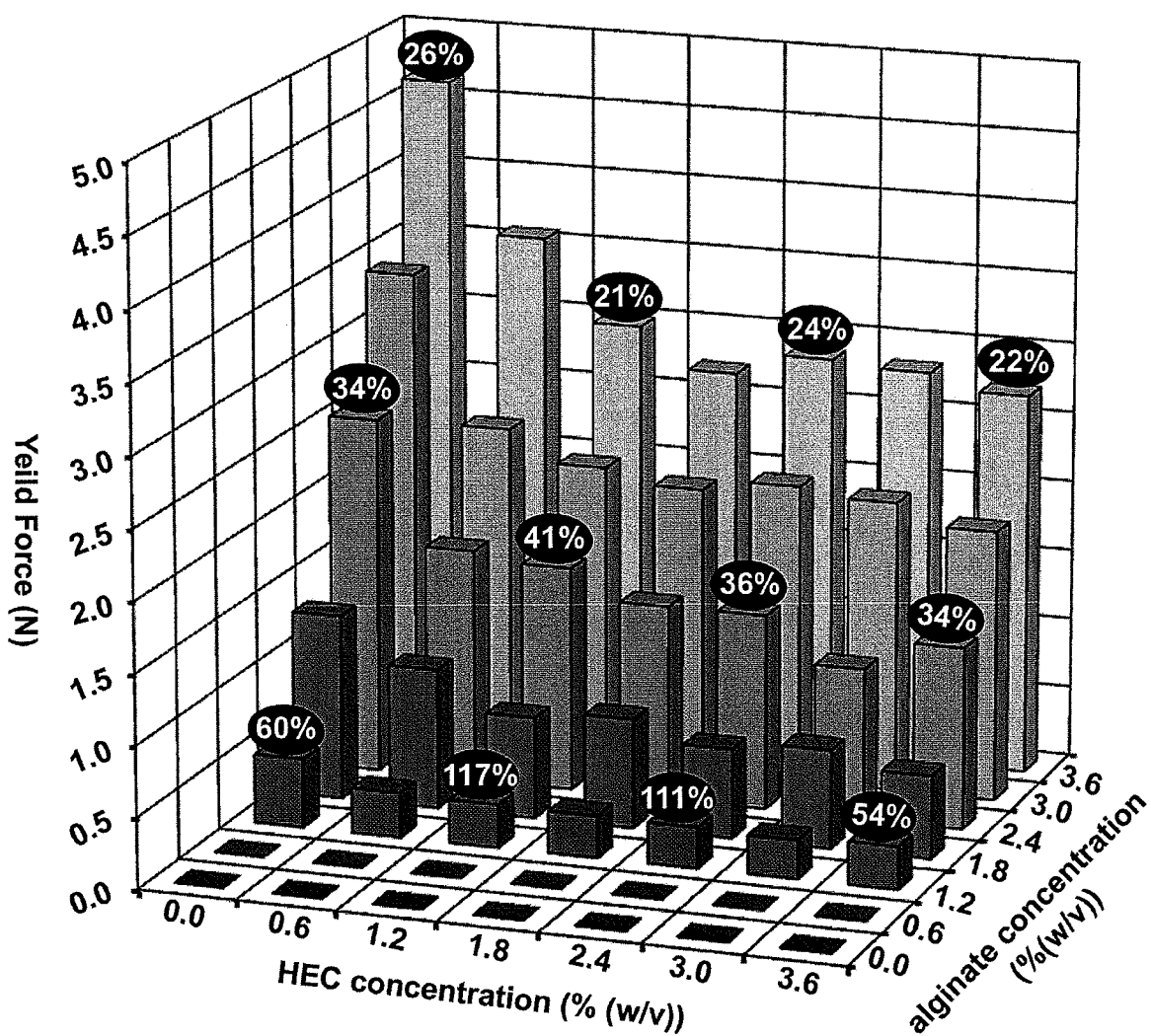
FIG. 11. Corneal epithelial cell viability in HEC-modified alginate gel discs correlations with the mechanical properties of gels. The viability of HCE cells extracted from alginate or HEC-modified alginate gel discs was assessed by Trypan blue exclusion. Proportions of live cells were expressed as a percentage of total cells (100%) initially encapsulated within gels (highlighted in black circles). The compressive moduli of gels was obtained by measuring their yield point with a trigger force of 0.0005 N. Data points for cell viability represent the mean (n=3) percentage live cells extracted and data points for compressive moduli represent 10 individual measurements.

Example 8: Analysis of the Compressive Mechanical Moduli of Calcium Alginate/HEC Hydrogels Gel spheres were formed by dispensing 2 mL alginate or alginate/HEC solutions dropwise into 30 mL CaCl$_2$ (100 mM). Gelled spheres were mechanically tested at 1, 5, 10, 15, 20, 25, 30, 45 and 60 min to determine the time periods needed for complete gelation. Alginate and alginate/HEC solutions gelled into stable gels after 10-20 min exposure to 102 mM CaCl$_2$. Mechanical testing of gels was achieved by compressing these structures using a TA.XT.plus Texture Analyser (Stable Micro Systems, Surrey, UK) with a 5 kg load cell and a P/1 KS flat ended stainless steel probe (Stable Micro Systems, Surrey, UK) with a 1 cm$^2$ surface area. Measurement of the force was taken, with a trigger force of 0.0005 N, and the yield point of gel spheres (point at which the gels split) was recorded. Force was recorded as the mechanical limit of the gels, described as comparative yield force and 10 measurements of each gel sample were performed. The results are shown in FIG. 11.

Example 9: Use of Alginate Hydrogel as a Stem Cell Transportation Device

Materials and Methods
Culture of Mouse Embryonic Stem Cells
Mouse embryonic stem cells (mESC) were cultured in Dulbecco's modified eagle's medium (DMEM) (Stemcell technologies, U.K.), supplemented with 10% fetal bovine serum (FBS) (Stemcell technologies, U.K.), 0.2% 2-mercaptoethanol (Life technologies, U.K.), 1% nonessential amino acid (Stemcell technologies, U.K.), 10 µg/ml leukemia inhibitor factor (LIF) (Stemcell technologies), 100 IU/ml penicillin and 100 mg/ml streptomycin (Invitrogen), in 0.1% gelatin (Life technologies, U.K.) coated T75 flasks (Greiner CellStar®, U.K.) at 37° C. under 5% $CO_2$ and 95% humidity. Cells were replenished with fresh medium every 3 days and grown to 70-80% confluence.

Culture of Human Mesenchymal Stem Cells

Human mesenchymal stem cells (hMSC) were cultured in low glucose DMEM (Life technologies, U.K.), supplemented with 10% FBS (Life technologies, U.K.), 100 IU/ml penicillin and 100 mg/ml streptomycin (Life technologies, U.K.), at 37° C. under 5% $CO_2$ and 95% humidity. Cells were replenished with fresh medium every 3 days and grown to 70-80% confluence.

Encapsulation of Mesenchymal and Embryonic Cells in Strontium Alginate Gel Discs $3 \times 10^5$ (viable cells) of hMSC were suspended in 1.2% (w/v) sodium alginate solution with 1.2% (w/v) HEC, or $3 \times 10^5$ (viable cells) of mESC were suspended in 1.2% (w/v) sodium alginate solution, before gelling into discs using 102 mM $SrCl_2$. Gel discs were formed by pipetting 2 mL sodium alginate/cell solutions into approximately 10 mL 102 mM $SrCl_2$ and using chromatography paper molds (Whatman) immersed in 102 mM $CaCl_2$ respectively. Briefly, to form gel discs, a paper ring with a 2 cm diameter opening was placed over a 3 cm diameter paper disc. A nylon mesh square with dimension of 1.5 cm×1.5 cm was immersed in 102 mM $SrCl_2$ and then placed in the centre of the paper ring to avoid breakup of gel during storage. These were saturated with 102 mM $SrCl_2$ before alginate or alginate/HEC solution (430 µL) containing either hMSC's or mESC's respectively was pipetted into the space within the ring. A second 3 cm diameter paper disc saturated with 102 mM $SrCl_2$ was placed over the alginate/paper assembly. Alginate or alginate/HEC solutions were exposed to 102 mM $SrCl_2$ for 5 min to allow complete gelation.

The subsequently formed strontium crosslinked alginate discs of 2 cm diameter containing cells were removed from the paper mold and suspended in supplemented DMEM medium within a sealed cryo vial. The gels were then stored at room temperature (18-22° C., atmospheric $CO_2$) for 5 days without medium change (n>9).

Cryopreservation of mESC and hMSC

Viable mESC and hMSC were centrifuged at 1500 rpm for 5 mins and followed resuspended in freezing medium (50% of mESC or hMSC supplement DMEM, 40% of fresh DMEM and 10% dimethyl sulfoxide (DMSO) (Fisher scientific, U.K.). Each of mESC and hMSC were equally aliquot into cryogenic storage vials (Fisher scientific, U.K.), with final concentration of $3 \times 10^5$ cells per vial (n>6). Cryogenic vials were transferred into Mr. Frosty (Fisher scientific, U.K.) containing of 100 ml of isopropyl alcohol (Fisher scientific, U.K.) and placed into −80° C. freezer for overnight to allow cells slowly frozen at 1° C./minute. Finally, Cryogenic vials were transferred into liquid nitrogen for 5 days storage.

Nuclear Staining to Analysis of Cell Distribution in HEC-Modified Strontium Alginate Gel Discs hMSC and mESC were encapsulated in strontium alginate (1.2% alginate) or HEC-modified calcium alginate (1.2% alginate/1.2% HEC) gel discs. Gels were embedded in OCT (TissueTek), frozen and cryosectioned. Transverse sections of gels were mounted on glass slides with Vectorshield containing PI fluorescent stain to visualise cell nuclei. Sections were observed by fluorescence microscopy (Carl Zeiss Meditec, Germany).

Cell Viability Analysis

Cells were extracted from alginate gel discs by incubation for 4 mins in alginate-dissolving buffer (0.15M NaCl, 0.055M sodium citrate) with gentle agitation. A Trypan blue exclusion assay was performed by mixing a 10 µL of the resulting cell suspension with 10 µL Trypan blue dye solution (v/v), before counting live (unstained) and dead (stained-blue) cells using a haemocytometer.

Microscopy

Microscopy images were obtained with a Nikon Eclipse TE200-U (Nikon, Japan) colour and fluorescence camera with magnification of 10×.

mESC and hMSC Growth Rate

The mESC and hMSC extracted from alginate after 5 days storage were cultured in supplemented DMEM for approximately 9 days to monitor the ability of these cells to attach and form colonies post-extraction and compare growth rate with cryopreserved cells. Data from individual growth curves were used to calculate the doubling time via www-.doubling-time.com.

Isolation of RNA and cDNA Synthesis

Total RNA was isolated using the TRI reagent (Sigma, Poole, U.K.) from both mESC and hMSC cells stored either by alginate gel encapsulation or cryopreserved in liquid nitrogen for 5 days according to the manufacturer's protocol. Total RNA was quantified spectrophotometrically (NanoDrop 2000, Thermo scientific, U.K.), and 1 µg RNA was reverse-transcribed using Revert Aid H Minus First Strand cDNA synthesis Kit (Fermentas, U.K.), following the manufacturer's protocol.

Gene Expression Analysis

Expression levels of mouse Oct-4 and SSEA-1, human CD90, CD73 and STRO-1 selected genes were determined along with mouse/human GAPDH as a reference gene. Primers for all the genes were designed using sequences obtained from the public domain. RT-PCR was carried out in triplicate with input of 10 ng cDNA per reaction using Sybr Green Dye (QIAGEN, U.K.) chemistry on the ABI 7900 (Applied Biosystem, U.K.) sequence detection system. Total reaction volume was 14 µl. Pre-incubation and initial denaturation of the template cDNA was performed at 95° C. for 10 min, followed by amplification for 40 cycles with 95° C. for 15 sec and 60° C. for 1 min. The test genes were normalized relative to the mean CT value of the reference genes.

Expression levels of the test genes were calculated relative to their expression in cells stored in gel. Gene expression calculations were done using standard and established methods to get the fold change in expression patterns.

Flow Cytometry Analysis for mESC Markers

The percentage of mESC expressing lineage specific markers was determined using mouse embryonic stem cell multi-colour flow cytometry kit (R&D system, U.K.), according to the manufacturer's protocol. In brief, mESC were harvested following four different treatments. 1. Immediately after extraction from alginate gel following 5 days storage; 2. Immediately after defrosting following liquid nitrogen storage; 3. After 10 days in standard culture conditions (37° C., 5% $CO_2$) following extraction from alginate gels and 4. After 10 days in standard culture conditions following liquid nitrogen storage followed by 10 days culturing in incubator. Following each treatment, mESC were washed twice by PBS in 2% fetal bovine serum, resuspended in 0.5 mL of fixation/permeablization buffer and incubated on ice for 30 minutes. Cells were gently vortexed intermittently in order to maintain a single cell suspension. Cells were then centrifuged, and the cell pellet resuspended in 200 µl of the permeabilization/wash buffer, at which point 10 µl of Sox2-PE, Oct3/4-APC, SSEA-1-PerCP, SSEA-4-FL1 antibodies or each corresponding isotype control antibody was added to the cells, and then incubated for 30-45 minutes on ice in the dark. Following the incubation, excess antibody was removed by washing the cells in 2 ml permeabilization/wash buffer; the final cell pellet was resuspended in 400 µl of PBS for flow cytometric analysis. Flow cytometry was performed using BD FACSCanto II cytometer (BD bioscience, USA).

Statistical Analysis

Unpaired Student's t-tests were performed using Microsoft Excel. QPCR and flow cytometry results are presented as the mean of 3 individual experiments with standard error of mean and P-value 0.05 considered significant.

Results

Cell Encapsulated Inside Aliginate Gel

Figure 12:
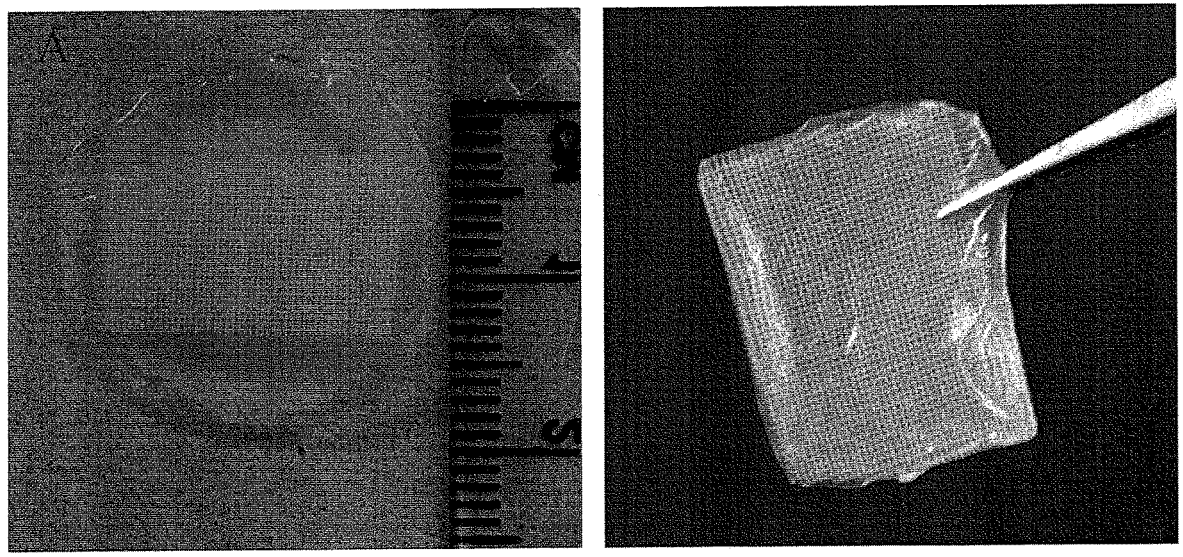
FIG. 12. Picture of calcium alginate gel disc (1.2%) with nylon mesh inside. Alginate gel disc is approximately 20 mm in length (A), and is readily transferred by forceps (B).

The composite gel, comprised of an alginate gel for cell encapsulation containing a nylon mesh, showed increased mechanical properties (FIG. 12).

Figure 13:
FIG. 13. hMSC and mESC were found to be evenly distributed within the strontium alginate gel as shown by propidium iodide nuclear staining.

Cell density and distribution of hMSC and mESC following encapsulation within the alginate-nylon gels were shown to be similar, both showing an even distribution throughout the gel FIG. 13.

The Survival Status of hMSC and mESC Inside Strontium Alginate Gel Discs

To examine the suitability of a strontium alginate gel disc for preservation and storage of hMSC and mESC, the proportion of viable cells retrieved following encapsulation and storage were investigated.

Figure 14:
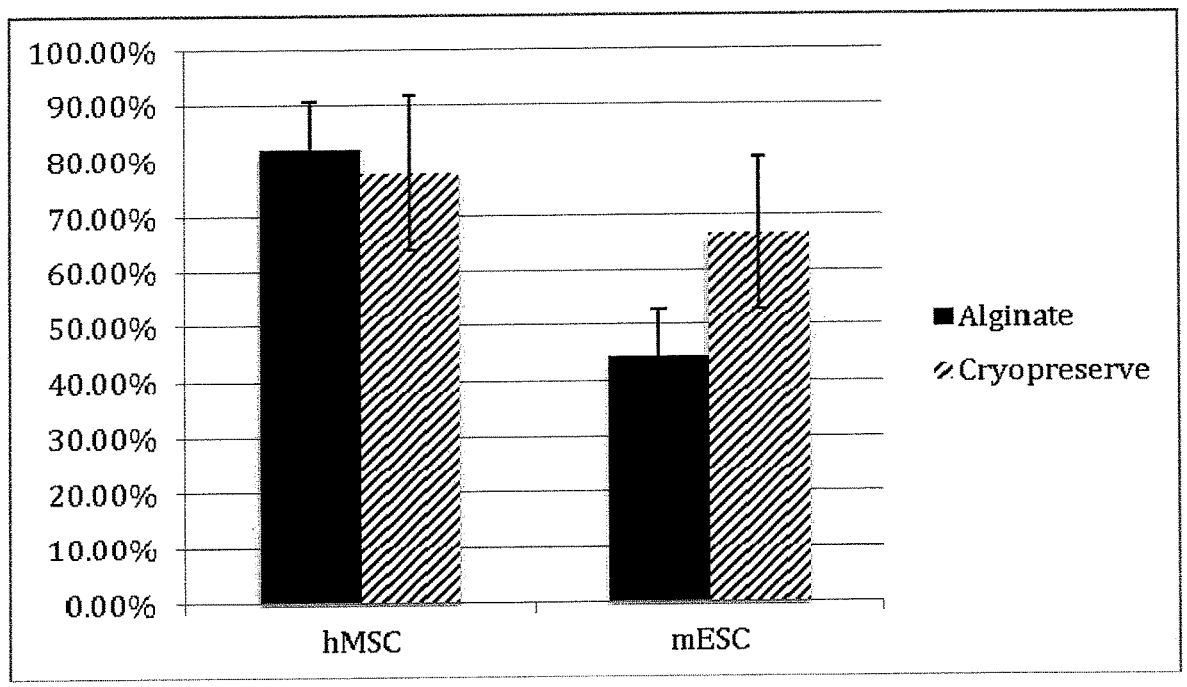
FIG. 14. The percentage of total cell survival following storage in either alginate-nylon gel discs or cryopreservation. Error bars represents standard deviation.
Figure 15:
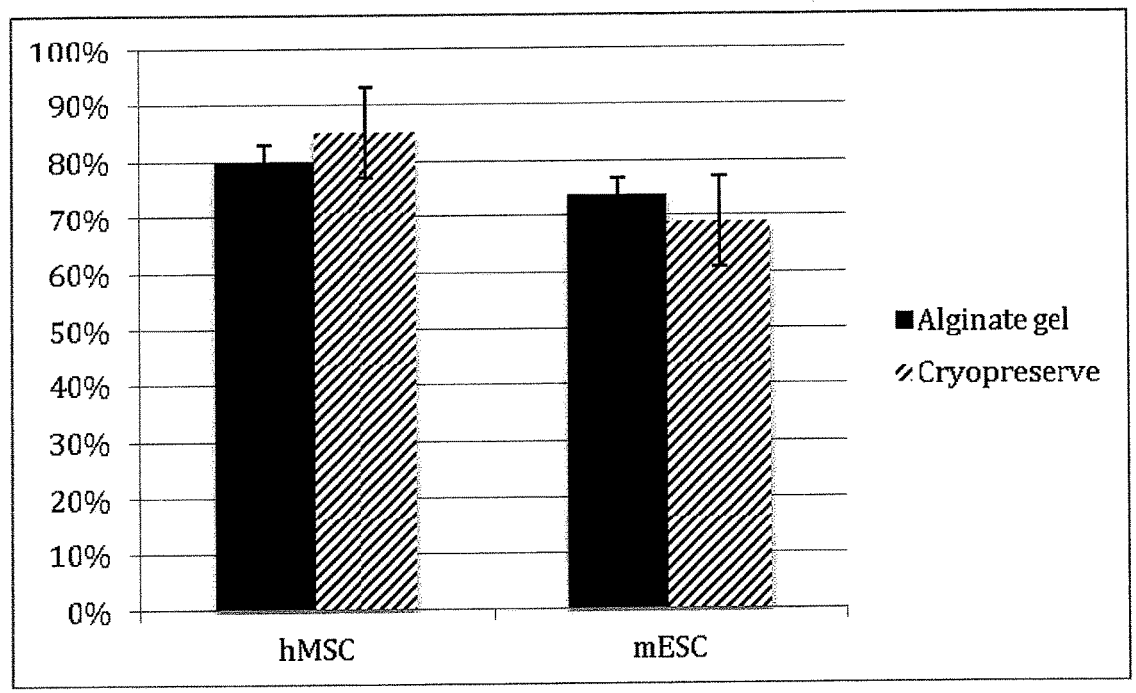
FIG. 15. The percentage of relative cell survival following storage in either alginate-nylon gel discs or cryopreservation. Error bars represents standard deviation.

After a 5-day storage period, the proportion of live cells retrieved following alginate encapsulation or cryopreservation were compared between hMSC and mESC (FIG. 14 and FIG. 15). The number of viable hMSC retrieved from alginate gel discs (82.22%) was slightly higher than those retrieved following cryopreservation (77.78%); in contrast, mESC stored inside alginate gel did not maintain the same level of viability (44.44%), the number retrieved following cryopreservation was similar to hMSC (74%) (FIG. 14).

In terms of the proportion of relative cell survival (i.e. not including cells that have been lost during the storage process) the two different storage conditions for both hMSC and mESC provided a similar level. Approximately 80% of the retrieved hMSC from alginate-nylon gels were viable, 5% lower than the cryopreserved hMSC. However, mESC stored inside alginate gel discs actually showed increased proportion of initial encapsulated cells (74%) than cryopreserved mESC (69%) (FIG. 15).

Survival Status of hMSC and mESC Post-Extraction

Figure 16:
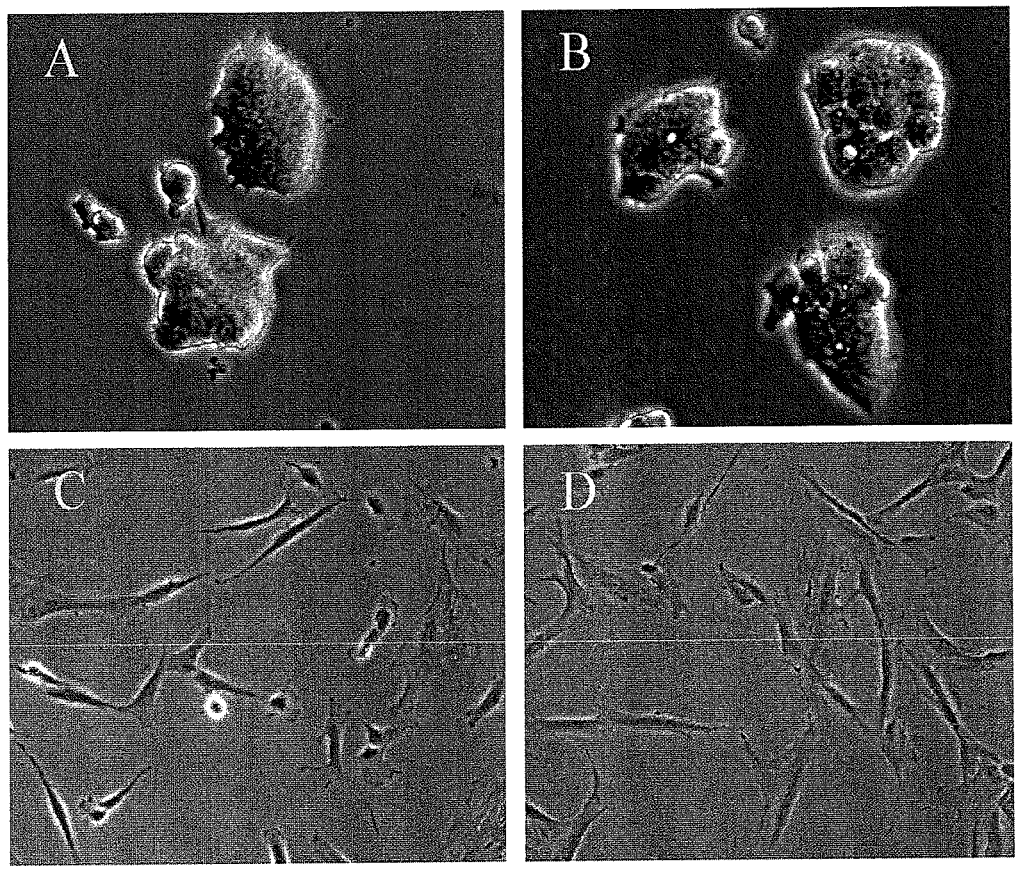
FIG. 16. Comparison between mESC and hMSC prior to encapsulation and following extraction from alginate gels after 5 days encapsulation. mESC colonies were found under both conditions prior to encapsulation (A), and following alginate gel encapsulation (B). Spindle shaped hMSC also showed no notable differences prior to (C) or following (D) encapsulation.
Figure 17:
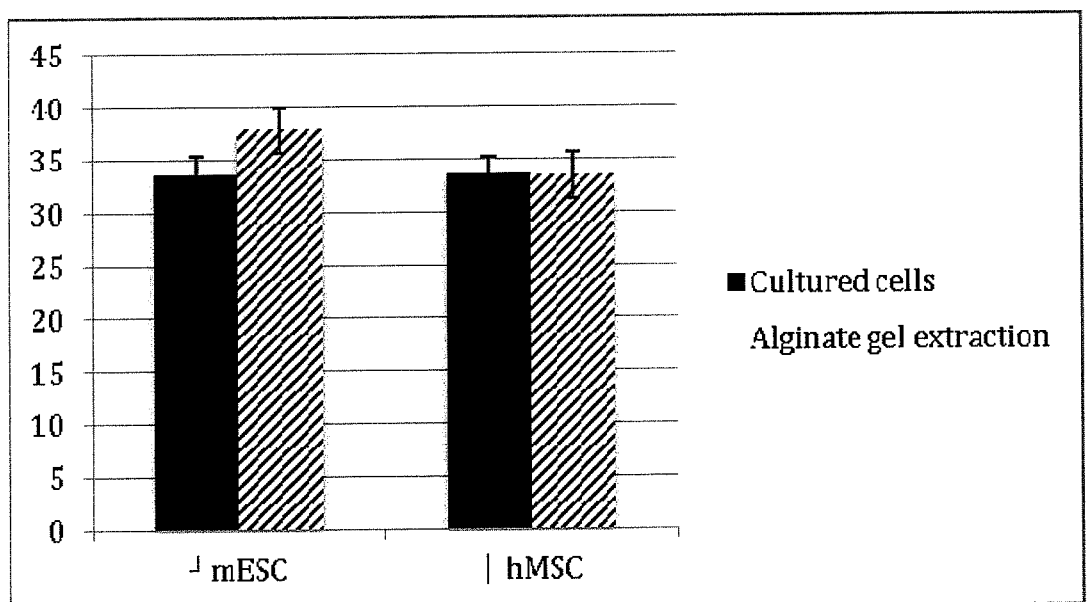
FIG. 17. Cell-doubling time (hours). No significant differences were seen between either hMSC or mESC prior and following gel encapsulation. Unit of x-axis: hours.

To further evaluate the cells' growth following extraction from strontium alginate-nylon gel storage, cell-doubling assays were performed on the extracted hMSC and mESC. Post-extracted culture of both hMSC and mESC at 37° C. under 5% $CO_2$ and 95% humidity demonstrated that cells from alginate gel discs were still capable of assembling into colonies (FIG. 16). More importantly, extracted cells not only survived, but also maintained similar proliferation rates. Cell doubling measurements clearly showed no significant difference between untreated cultured cells and those extracted from calcium alginate gel discs (FIG. 17) using the same passage number and initial seeding density.

Expression of Common Cell Markers Following Extraction from Strontium Alginate-Nylon Gels after 5 Days Storage.

Figure 18:
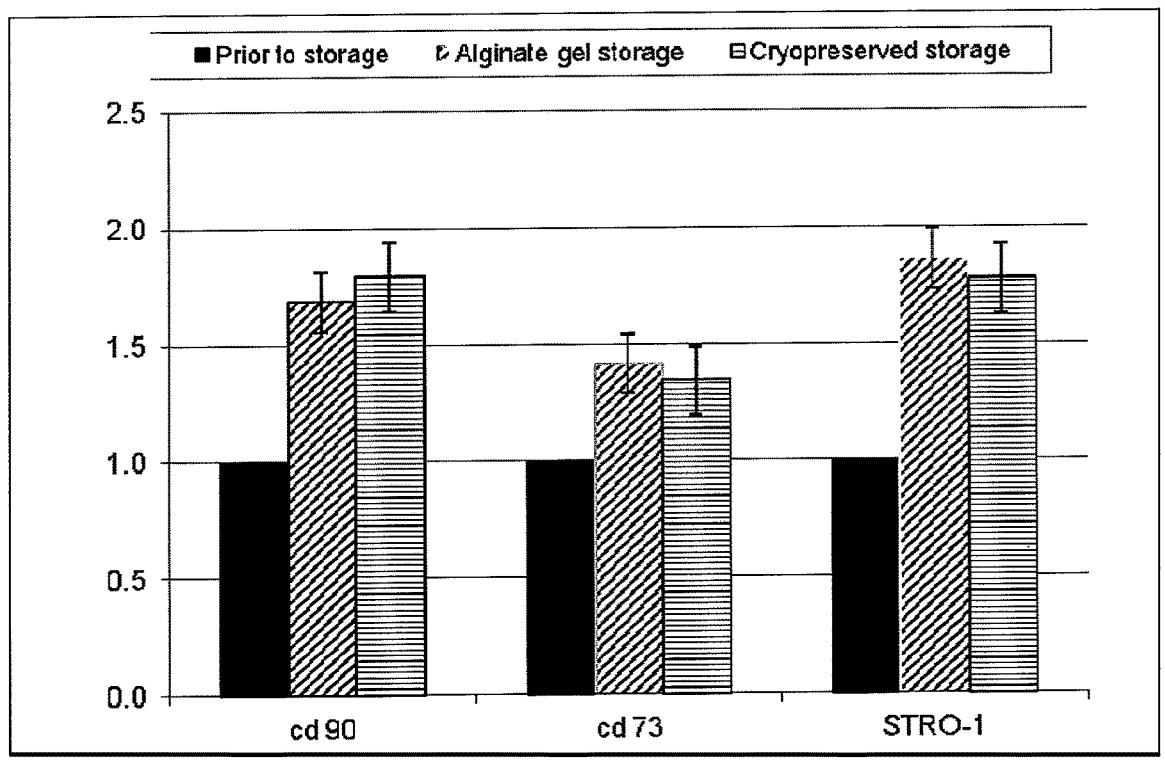
FIG. 18. hMSC markers detection of hMSC in optimal culture condition, preserved in alginate gel condition and cryopreservation condition. All three of MSC markers showed increased mRNA level after alginate and cryopreservation storage.
Figure 19:
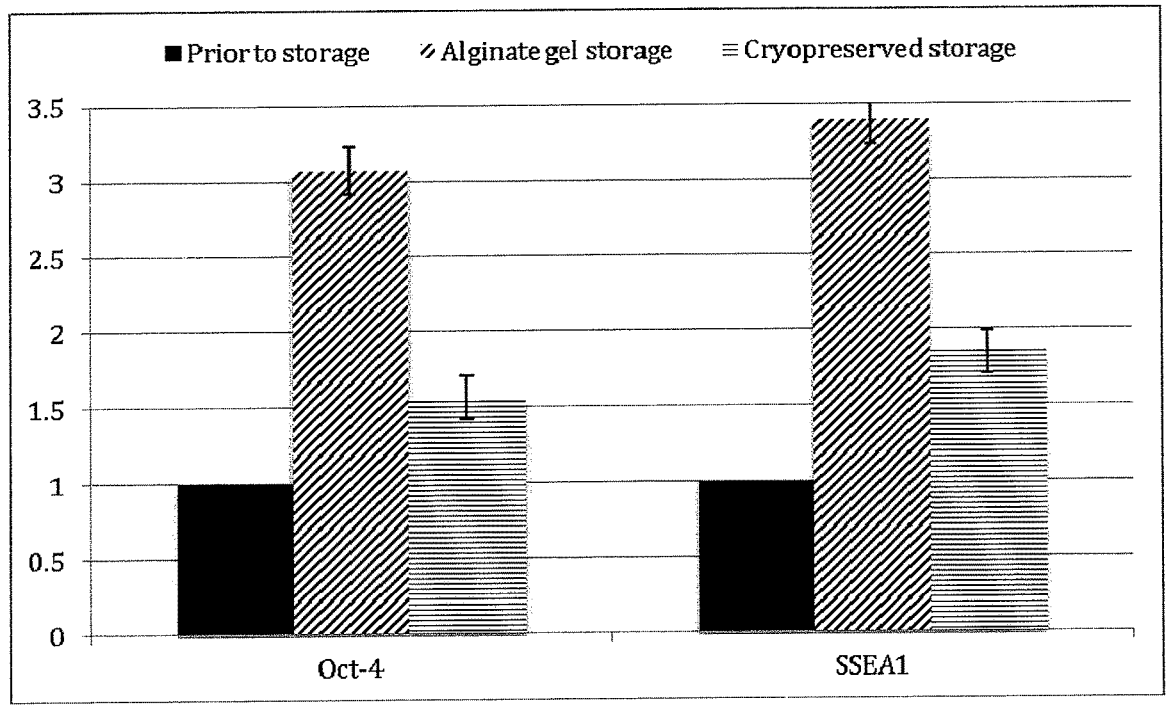
FIG. 19. mESC markers detection of mESC in optimal culture condition, preserved in alginate gel condition and cryopreservation condition. mESC extracted from alginate gel showed relatively highest value of both Oct-3/4 and SSEA1 markers.

To validate the cells phenotype after storage within strontium alginate gel at room temperature, a number of robust stem cell markers were examined. Quantitative PCR analyses were performed on hMSC and mESC before and after 5 days in storage within either alginate gel discs or cryopreservation. Both mesenchymal and embryonic cell markers were examined respectively. The QPCR results showed no sign of decreasing levels of common hMSC and mESC stem cell markers (FIG. 18 and FIG. 19). Interestingly, mRNA levels of both hMSC (CD90, CD73 and STRO-1) and mESC markers (Oct-4 and SSEA-1) actually increased after 5 days storage both inside alginate gels and in liquid nitrogen (cryopreservation). mRNA levels of hMSC markers from cells stored inside alginate gels were very close to cells stored in liquid nitrogen. Surprisingly, for mESC stored inside alginate gel, both Oct-4 and SSEA-1 mRNA levels were two fold higher than from cryopreserved mESC.

Figure 20:
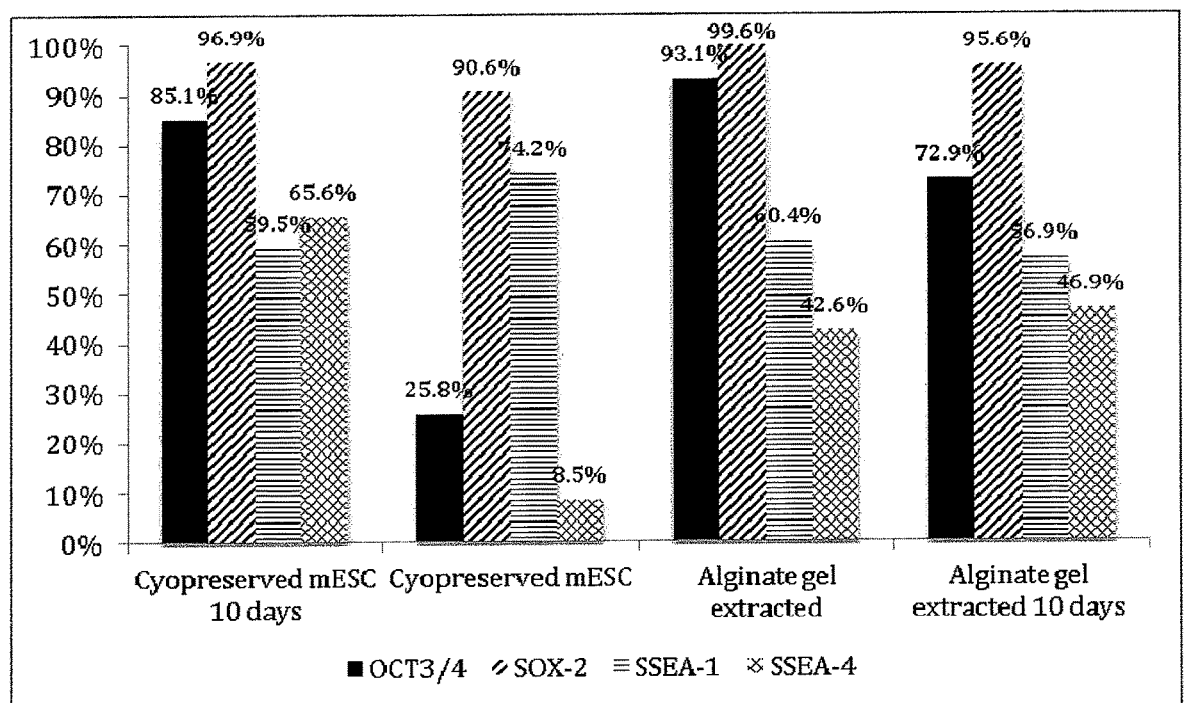
FIG. 20. Expression of mESC markers between mESC encapsulated within alginate gel and cryopreserved in liquid nitrogen by flow cytometry. mESC's were studied immediately following release form a 5 day storage (alginate or cryopreservation). Cells were also studied following 10 days in standard culture media post-storage. Cryopreservation resulted in a considerable, albeit temporary loss of OCT3/4 and SSEA4 expression. No difference was seen between alginate-encapsulated cells.

Flow cytometry was performed against four specific mESC markers following either storage for 5 days (in either alginate gel or liquid nitrogen) or 10 days incubation at 37° C. under 5% $CO_2$ and 95% humidity (of previously cryo- or gel-stored cells). Following storage, expression of OCT 3/4 and SSEA4 was significantly decreased by cryo-preservation but following 10 days in optimal culture conditions they increased to levels similar to those seen in the alginate encapsulated cells. Interestingly the expression of each marker remained stable following gel encapsulation, suggesting cells could be used immediately following release from the gel (FIG. 20).

Example 10: Storage of Different Cell Types

Figure 21:
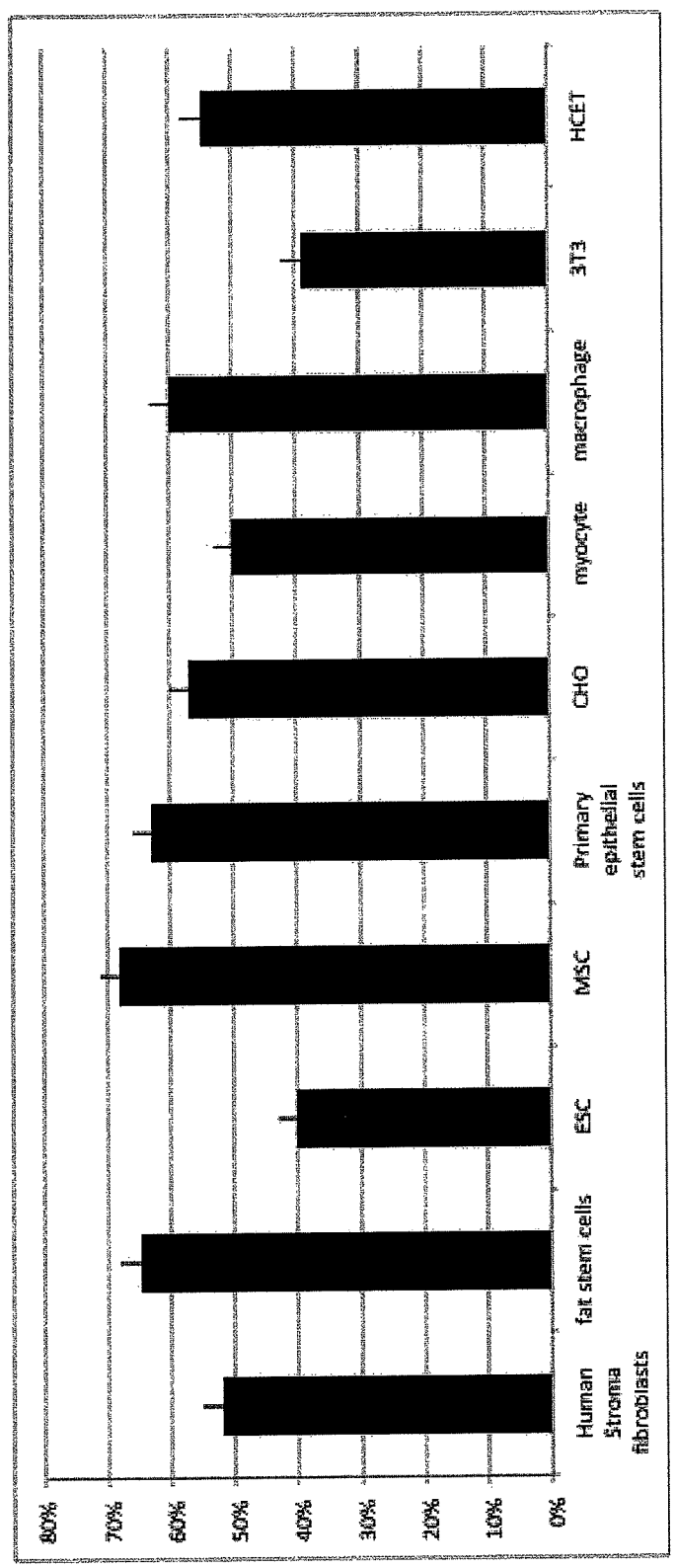
FIG. 21. Total cell viability (viable cells extracted/total number encapsulated) following 5 days at ambient storage. Results show success across a range of cell types including immortalised cell lines, primary cells and stem cells.

A number of different cell types were stored in a 1.2% alginate gel disc at ambient conditions for 5 days. The results showed high viability levels after storage across a range of different cell types including immortalised cell lines, primary cells lines and stem cells (FIG. 21).

The invention claimed is:
1. A packaged composition comprising:
   (a) a 0.5%-1.3% calcium or strontium alginate hydrogel in the form of a thin layer or disc, wherein the hydrogel comprises pores of 0.1-3.0 µm in diameter;
   (b) a population of living cells, the living cells being entrapped or encapsulated within the hydrogel; and
   (c) a packaging, the packaging being a water-tight or air-tight material suitable for transportation from a first location to a second location, wherein the second location is at least one mile from the first location, and the hydrogel is enclosed within the packaging;
   wherein the hydrogel and the living cells entrapped or encapsulated therein are in a state of storage in the packaging from 1 day up to 20 weeks;
   wherein cell division, and optionally cell differentiation, of all or a substantial proportion of the living cells which are entrapped or encapsulated within the hydrogel is suppressed or prevented.

2. A packaged composition as claimed in claim 1, wherein the hydrogel comprises detectable levels of a water-soluble pore size increasing agent; and wherein the hydrogel is obtained by a process, comprising:
   (i) gelling a hydrogel-forming polymer in the presence of living cells and a water-soluble pore size increasing agent; and
   (ii) dissolving a substantial proportion of the pore size increasing agent out of the hydrogel;
   wherein the hydrogel is formed by a calcium or strontium alginate gel.

3. The packaged composition as claimed in claim 1, wherein the hydrogel is a 1.1-1.3% strontium alginate hydrogel.

4. The packaged composition as claimed in claim 1, wherein the hydrogel is about 0.6% or about 1.2% calcium or strontium alginate hydrogel.

5. The packaged composition as claimed in claim 1, wherein the hydrogel has a thickness of 0.1-5.0 mm.

6. The packaged composition as claimed in claim 1, wherein the living cells are released from the hydrogel at the second location.

7. The packaged composition as claimed in claim 2, wherein the water-soluble pore size increasing agent comprises hydroxyethyl cellulose (HEC).

8. The packaged composition as claimed in claim 1, wherein the living cells remain at least 50% viable during transportation from a first location to a second location at a temperature of up to 30° C.

9. The packaged composition as claimed in claim 1, wherein the state of storage in the packaging is at ambient temperature.

10. The packaged composition as claimed in claim 1, wherein the living cells remain at least 50% viable after 3 days storage at ambient storage conditions.

* * * * *